US010676443B2

(12) United States Patent
Schirmer et al.

(10) Patent No.: US 10,676,443 B2
(45) Date of Patent: Jun. 9, 2020

(54) METHOD FOR PRODUCING (4S)-4-[4-CYANO-2-(METHYLSULFONYL) PHENYL]-3,6-DIMETHYL-2-OXO-1-[3-(TRIFLUOROMETHYL)PHENYL]-1,2,3,4-TETRAHYDRO PYRIMIDINE-5-CARBONITRILE

(71) Applicant: pH Pharma Co., Ltd., Seoul (KR)

(72) Inventors: Heiko Schirmer, Solingen (DE); Philipp Rubenbauer, Dusseldorf (DE); Birgit Keil, Dusseldorf (DE); Britta Olenik, Bottrop (DE)

(73) Assignee: pH Pharma Co., Ltd., Seoul (KR)

( * ) Notice: Subject to any disclaimer, the term of this patent is extended or adjusted under 35 U.S.C. 154(b) by 0 days.

(21) Appl. No.: 16/394,811

(22) Filed: Apr. 25, 2019

(65) Prior Publication Data

US 2019/0248750 A1 Aug. 15, 2019

Related U.S. Application Data

(62) Division of application No. 15/559,385, filed as application No. PCT/EP2016/055498 on Mar. 15, 2016, now Pat. No. 10,316,001.

(30) Foreign Application Priority Data

Mar. 18, 2015 (EP) .................... 15159570

(51) Int. Cl.
*C07D 239/22* (2006.01)
*C07C 315/00* (2006.01)

(52) U.S. Cl.
CPC .......... *C07D 239/22* (2013.01); *C07C 315/00* (2013.01); *C07B 2200/13* (2013.01)

(58) Field of Classification Search
CPC .................................................. C07D 239/22
See application file for complete search history.

(56) References Cited

U.S. PATENT DOCUMENTS

| 5,532,366 | A  | 7/1996  | Edwards et al. |
| 7,566,723 | B2 | 7/2009  | Gielen-Haertwig et al. |
| 7,687,510 | B2 | 3/2010  | Gielen-Haertwig et al. |
| 7,691,854 | B2 | 4/2010  | Gielen-Haertwig et al. |
| 7,893,073 | B2 | 2/2011  | Gielen-Haertwig et al. |
| 8,288,402 | B2 | 10/2012 | Von Nussbaum et al. |
| 8,580,800 | B2 | 11/2013 | Von Nussbaum et al. |
| 8,691,817 | B2 | 4/2014  | Von Nussbaum et al. |
| 8,889,700 | B2 | 11/2014 | Von Nussbaum et al. |
| 9,174,997 | B2 | 11/2015 | Von Nussbaum et al. |
| 2008/0021053 | A1 | 1/2008 | Gielen-Haertwig et al. |
| 2008/0064704 | A1 | 3/2008 | Gielen-Haertwig et al. |
| 2010/0010024 | A1 | 1/2010 | Von et al. |
| 2010/0184788 | A1 | 7/2010 | Gielen-Haertwig et al. |
| 2018/0072685 | A1 | 3/2018 | Schirmer et al. |

FOREIGN PATENT DOCUMENTS

| WO | 2001040231 A1 | 6/2001 |
| WO | 2004024700 A1 | 3/2004 |
| WO | 2005009392 A2 | 2/2005 |
| WO | 2005082863 A2 | 9/2005 |
| WO | 2005082864 A1 | 9/2005 |
| WO | 2006082412 A2 | 8/2006 |
| WO | 2006136857 A1 | 12/2006 |
| WO | 2007042815 A1 | 4/2007 |
| WO | 2007129060 A1 | 11/2007 |
| WO | 2008030158 A1 | 3/2008 |
| WO | 2009080199 A1 | 7/2009 |

OTHER PUBLICATIONS

Barnes, P., "Chronic Obstructive Pulmonary Disease", The New England Journal of Medicine 343(4), 269-280 (2000).
Chollet-Martin, S., et al., "Interactions Between Neutrophils and Cytokines in Blood and Aleolar Spaces During ARDS", Am J Respir Crit Care Med 153, 594-601 (1996).
Cowan, K., et al., "Complete reversal of fatal pulmonary hypertension in rats by a serine elastase inhibitor", Nature Medicine 6(6), 698-702 (2000).
D'Alonzo, G., et al., "Survival in Patients with Primary Pulmonary Hypertension", Annals of Internal Medicine 115, 343-349 (1991).
Edwards, J., et al., "In vitro inhibition of human neutrophil elastase by oleic acid albumin formulations from derivatized cotton wound dressings", International Journal of Pharmaceutics 284, 1-12 (2004).
Elssner, A., et al., "The role of neutrophils in the pathogenesis of obliterative bronchiolitis after lung transplantation", Transpl Infect Dis 3, 168-176 (2001).
Fujie, K., et al., "Inhibition of elastase-induced acute inflammation and pulmonary emphysema in hamsters by a novel neutrophil elastase inhibitor FR901277", Inflammation Research 48(3), 160-167 (1999).
Gadek, J., et al., "Antielastases of the Human Alveolar Structures", J Clin Invest 68, 889-898 (1981).
Ghofrani, H., et al., "Neue Therapieoptionen in der Behandlung der pulmonalarteriellen Hypertonie", Herz 30(4), 296-302 (2005).
Hill, A., et al., "Airways inflammation in chronic bronchitis: the effects of smoking and α1-antitrypsin deficiency", European Respiratory Journal 15, 886-890 (2000).
Humbert, M., et al., "Cellular and Molecular Pathobiology of Pulmonary Arterial Hypertension", Journal of American College of Cardiology 43(12) Supp S, 13S-24S (2004).
Ito, T., et al., "Current Drug Targets and Future Therapy of Pulmonary Arterial Hyper-tension", Current Medicinal Chemistry 14, 719-733 (2007).
Janoff, A., "State of the Art-Elastases and Emphysema, Current Assessment of the Protease-Antiprotease Hypothesis", Am Rev Respir Dis 132, 417-433 (1985).

(Continued)

*Primary Examiner* — Brenda L Coleman
(74) *Attorney, Agent, or Firm* — Viksnins Harris Padys Malen LLP

(57) ABSTRACT

The invention relates to a new and improved method for preparation of (4S)-4-[4-cyano-2-(methyl sulfonyl)phenyl]-3,6-dimethyl-2-oxo-1-[3-(trifluoromethyl)phenyl]-1,2,3,4-tetrahydro pyrimidine-5-carbonitrile of formula (I), as well as the preparation and use of the crystal form (A) of (4S)-4-[4-cyano-2-(methylsulfonyl)phenyl]-3,6-dimethyl-2-oxo-1-[3-(trifluoromethyl)phenyl]-1,2,3,4-tetrahydro pyrimidine-5-carbonitrile of formula (I).

7 Claims, 2 Drawing Sheets

(56) References Cited

OTHER PUBLICATIONS

Kafienah, W., et al., "Cleavage of native type I collagen by human neutrophil elastase", Biochemical Journal 330(Pt 2), 897-902 (1998).
Kawabata, K., et al., "The role of neutrophil elastase in acute lung injury", European Journal of Pharmacology 451 (1), 1-10 (2002).
Liou, T., et al., "Nonisotropic Enzyme-Inhibitor Interactions: A Novel Nonoxidative Mechanism for Quantum Proteolysis by Human Neutrophils", Biochemistry 34, 16171-16177 (1995).
Luhr, O., et al., "Incidence and Mortality after Acute Respiratory Failure and Acute Respiratory Distress Syndrome in Sweden, Denmark, and Iceland", Am J Respir Crit Care Med 159, 1849-1861 (1999).
Meddahi, A., et al., "FGF protection and inhibition of human neutrophil elastase by carboxymethyl benzylamide sulfonate dextran derivatives", International Journal of Biological Macromolecules 18, 141-145 (1996).
Mirzaei, Y, et al., "Investigation the chemical reactivity of positions N-3, C-5 and C6-methyl group in biginelli type compounds and synthesis of new dihydropyrimidine derivatives", J Heterocyclic Chem 38, 1051-1054 (2001).
Nakamura, H., et al., "Neutrophil elastase in respiratory epithelial lining fluid of individuals with cystic fibrosis induces Interleukin-8 gene expression in a human bronchial epithelial cell line", Journal of Clinical Investigation 89(5), 1478-1484 (1992).
Patent Cooperation Treaty, International Searching Authority, Search Report and Written Opinion for PCT/EP2016/055498, 15 pages, dated Aug. 4, 2016.
Rabinovitch, M., "Comroe Lecture, EVE and beyond, retro and prospecitve insights", Am J Physiol 277, L5-L12 (1999).
Rabinovitch, M., "Molecular pathogenesis of pulmonary arterial hypertension", Journal of Clinical Investigation 122 (12), 4306-4313 (2012).
Rabinovitch, M., et al., "Pulmonary Artery Endothelial Abnormalities in Patients with Congenital Heart Defects and Pulmonary Hypertension", Laboratory Investigation 55(6), 632653 (1986).
Rosenzweig, E., "Emerging treatments for pulmonary arterial hypertension", Expert Opin Emerging Drugs 11(4), 609-619 (2006).
Simonneau, G., et al., "Clinical Classification of Pulmonary Hypertension", Journal of the American College of Cardiology 43(12), Suppl S, 5S-12S (2004).
Steinbrecher, T., et al., "Bornyl (3,4,5-trihydroxy)-cinnamate—an optimized human neutrophil elastase inhibitor designed by free energy calculations", Bioorganic & Medicinal Chemistry 16, 2385-2390 (2008).
Stockley, R., et al., "Neutrophils and Protease/Antiprotease Imbalance", Am J Respir Crit Care Med 160, S49-S52 (1999).
Todorovich-Hunter, L, et al., "Increased Pulmonary Artery Elastolytic Activity in Adult Rats with Monocrotaline-Induced Progressive Hypertensive Pulmonary Vascular Disease Compared with Infant Rats with Nonprogressive Disease", Am Rev Respir Dis 146, 213-223 (1992).
Von Nussbaum, F, et al., "Freezing the Bioactive Conformation to Boost Potency: The Identification of BAY 85-8501, a Selective and Potent Inhibitor of Human Neutrophil Elastase for Pulmonary Diseases", ChemMedChem 10, 1163-1173 (2015).
Werb, Z, et al., "Elastases and Elastin Degradation", Journal of Investigative Dermatology 79, 154s-159s (1982).
Zaidi, S, et al., "Overexpression of teh Serine Elastase Inhibitor Elan Protects Transgenic Mice From Hypoxic Pulmonary Hypertension", Circulation 105, 516-521 (2002).

Fig. 1: X-ray diffraction pattern of the compound of formula (I) in crystal form (A)
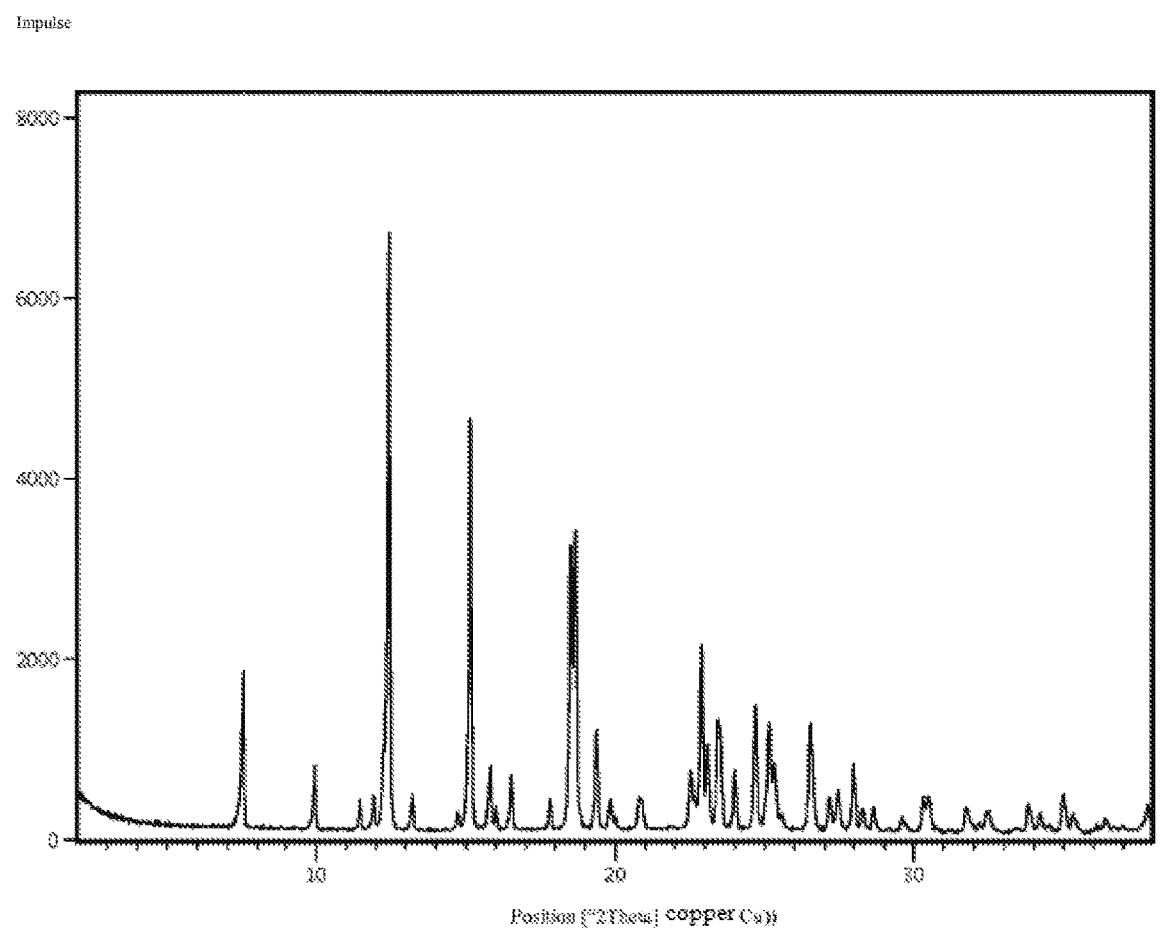

Fig. 2: Raman spectrum of the compound of formula (I) in crystal form (A)
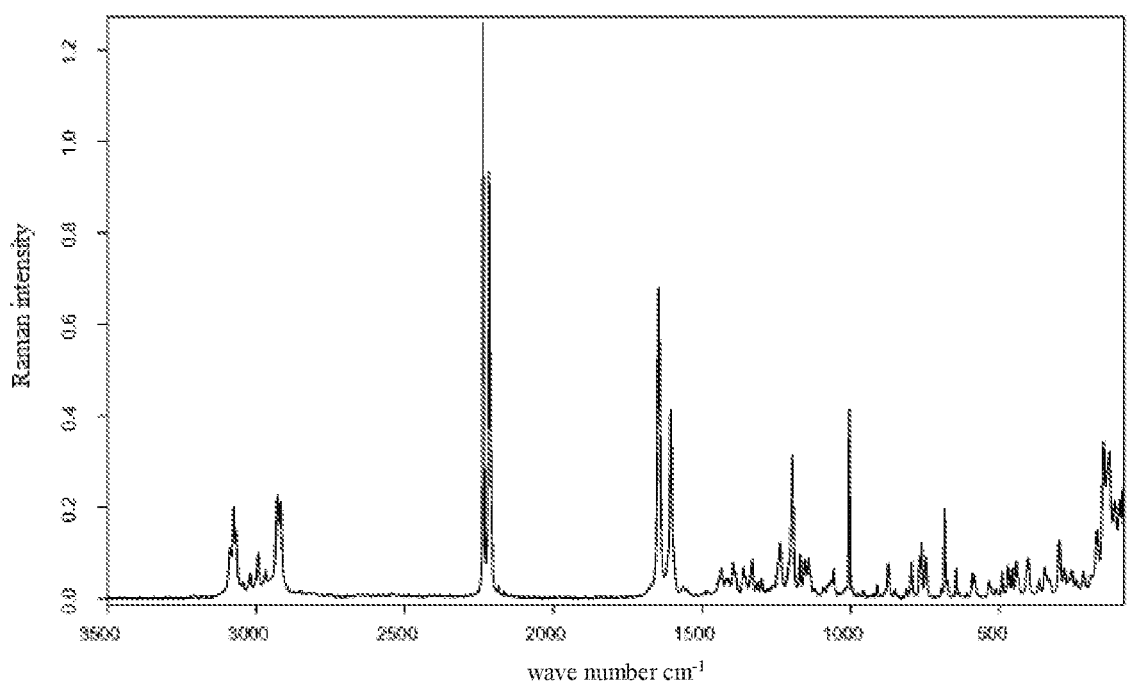

METHOD FOR PRODUCING (4S)-4-[4-CYANO-2-(METHYLSULFONYL)PHENYL]-3,6-DIMETHYL-2-OXO-1-[3-(TRIFLUOROMETHYL)PHENYL]-1,2,3,4-TETRAHYDRO PYRIMIDINE-5-CARBONITRILE

CROSS REFERENCE TO RELATED APPLICATIONS

This divisional application claims the benefit of priority to U.S. application Ser. No. 15/559,385, filed 18 Sep. 2017, which is a Section 371 application of International Application No. PCT/EP2016/055498, filed 15 Mar. 2016, which claims the benefit of priority to European Patent Application No. 15159570.9, filed 18 Mar. 2015, all of which are herein incorporated by reference in their entirety.

The invention relates to a novel and improved method for producing (4S)-4-[4-cyano-2-(methylsulfonyl)phenyl]-3,6-dimethyl-2-oxo-1-[3-(trifluoromethyl)phenyl]-1,2,3,4-tetrahydro pyrimidine-5-carbonitrile of formula (I), and to the production and use of the crystal form (A) of (4S)-4-[4-cyano-2-(methylsulfonyl)phenyl]-3,6-dimethyl-2-oxo-1-[3-(trifluoromethyl)phenyl]-1,2,3,4-tetrahydro pyrimidine-5-carbonitrile of formula (I).

Method for producing (4S)-4-[4-cyano-2-(methylsulfonyl)phenyl]-3,6-dimethyl-2-oxo-1-[3-(trifluoromethyl)phenyl]-1,2,3,4-tetrahydro pyrimidine-5-carbonitrile The present invention relates to improved methods for producing (4S)-4-[4-cyano-2-(methylsulfonyl)phenyl]-3,6-dimethyl-2-oxo-1-[3-(trifluoromethyl)phenyl]-1,2,3,4-tetrahydro pyrimidine-5-carbonitrile and its crystal form (A), which is used in the production of pharmaceuticals.

The compound (4S)-4-[4-cyano-2-(methylsulfonyl)phenyl]-3,6-dimethyl-2-oxo-1-[3-(trifluoromethyl)phenyl]-1,2,3,4-tetrahydro pyrimidine-5-carbonitrile is known from WO 2009/080199 A1 and corresponds to the formula (I)

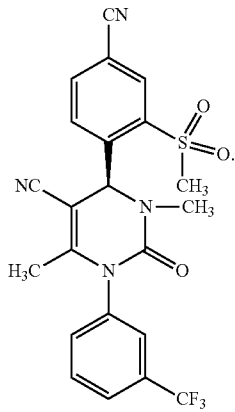

(I)

The compound of formula (I) is an inhibitor of human leukocyte elastase (HLE, EC 3.4.21.37), also known as human neutrophil elastase (HNE, hNE). Human leukocyte elastase belongs to the family of serine proteases. The proteolytic enzyme is found in the azurophilic granules of polymorphonuclear leukocytes (PMN leukocytes). The intracellular elastase plays an important role in defense against pathogens by breaking down foreign particles that are taken up through phagocytosis. Activated neutrophil cells release HNE from the granules into the extracellular space (extracellular HNE), a portion of the liberated HNE remaining on the outside of the neutrophil cell membrane (membrane-bound HNE). The highly active enzyme is able to break down a multitude of connective tissue proteins, such as the proteins elastin, collagen and fibronectin. Elastin occurs in high concentrations in all tissue types exhibiting high elasticity, such as in the lungs and in arteries. In a multitude of pathological processes (such as tissue damage), HNE plays a role in tissue breakdown and remodeling. Furthermore, HNE is an important modulator in inflammatory processes. For example, HNE induces a heightened gene expression of interleukin-8 (IL-8).

It is therefore presumed that HNE plays an important role in many illnesses, injuries and pathological alterations whose origin and/or progression are related to an inflammatory occurrence and/or proliferative and hypertrophic tissue and vessel remodeling. These may be, in particular, diseases and/or damage to the lungs or the cardiovascular system, or may involve sepsis, cancer illnesses, or other inflammatory diseases. HNE inhibitors are used especially in the treatment and/or prevention of diseases of the lungs and the cardiovascular system.

In WO 2009/080199 A1 a method is also described for producing the compound of formula (I), being regarded as the closest prior art. In this case, starting from 3-fluoro-4-methylbenzonitrile, the target compound (I) is produced in 10 steps with a total yield of 4.45% of theory. The compound is obtained by concentration of chromatography fractions as an amorphous solid; a defined crystallization method of the end stage to establish a defined crystal form has not yet been described.

The following scheme shows in detail the intermediate steps carried out in WO

Scheme 1

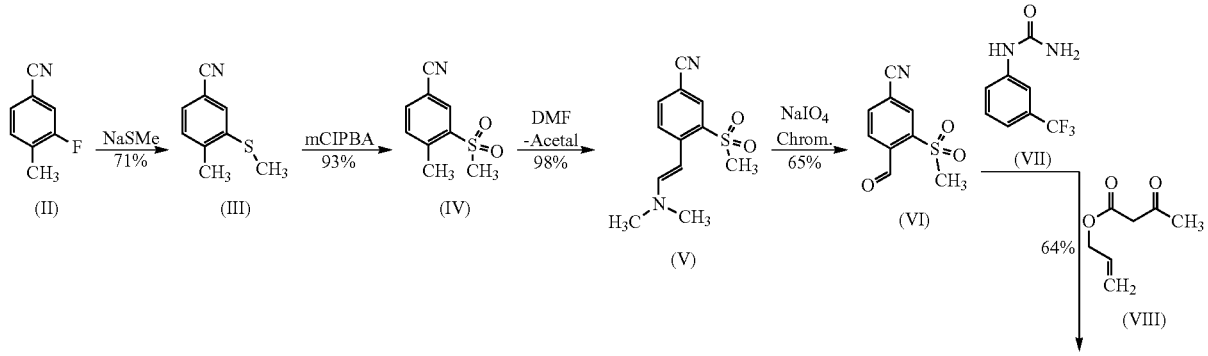

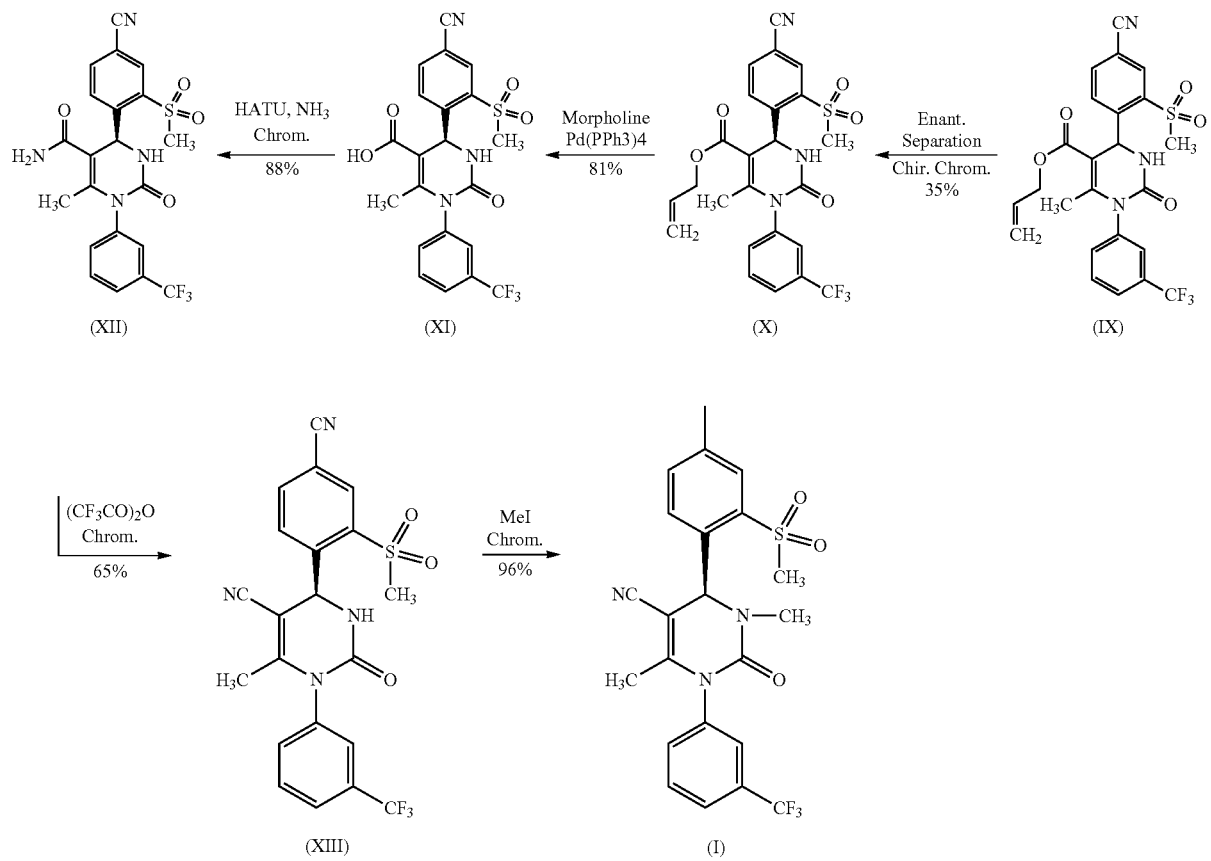

The above sketched reaction scheme is described in WO 2009/080199 A1 as follows: the reaction sequence from a compound of formula (II) through the compounds of formulas (III), (IV) and (V) to a compound of formula (VI) in scheme 6 and examples 1A, 2A method B, 3A method B and 4A method B; the reaction sequence from a compound of formula (VI) through a compound of formula (IX) to a compound of formula (X) in scheme 1 and examples 3 and 4; and the reaction sequence from a compound of formula (X) through the compounds of formulas (XI) and (XII) to a compound of formula (XIII) in scheme 2 and examples 5A, 5 and 6. The synthesis of the compound of formula (I) is described in example 33 method B.

Four chromatographic purifications are used, as along with one chiral chromatography step for the separating of the enantiomers (IX).

This method known from WO 2009/080199 A1 has various drawbacks in the management of the reaction, which have especially unfavorable effects during the production of the compound of formula (I) on a technical scale.

The overall yield at around 4.45% of theory is very low. Many steps occur in very high dilution and with very large reagent surpluses. Thus, in particular, the sequence for producing the nitrile-aldehyde intermediate 4-formyl-3-(methylsulfonyl)benzonitrile (VI), which has a central role in this synthesis, is not acceptable from an atomic-economic standpoint.

In the synthesis according to WO 2009/080199 A1, the racemic allyl ester of formula (IX) was separated by means of chiral chromatography into the enantiomers and the S-enantiomer (X) was isolated in a 35% yield. Such a chromatographic separation of the racemates is very cost and time intensive and is thus disadvantageous for synthesis on a large technical scale.

Furthermore, this method as described in WO 2009/080199 cannot be transferred to a technical scale, since on the one hand very costly reagents are used, such as trifluoroacetic acid anhydride and O-(7-azabenzotriazolo-1-yl)-N,N,N',N'-tetramethyluronium hexafluorophosphate (HATU). Trifluoracetic acid anhydride is used to convert the compound of formula (XII) into the compound of formula (XIII), HATU is used to convert the compound of formula (XI) into the compound of formula (XII). Nor does a process on technical scale allow the use of any toxic reagents. This is a disadvantage per se, and furthermore these toxic substances must be removed from the end product (I) to below the maximum allowable limit in the product for regulatory reasons, which means an additional expense. This is especially so for the alkylation with methyl iodide in fivefold excess as the last step in the synthesis sequence, since it must be assured that the alkylation reagent methyl iodide, recognized as being carcinogenic, is entirely purified out. The use of benzotriazoles such as HATU is also forbidden on a large technical scale for reasons of toxicity. Moreover, many intermediate chromatographic purifications are performed according to the method described in WO 2009/080199, which are generally very cost intensive. Therefore, there was a need for a practicable large technical scale synthesis that provides the compound of formula (I) in a reproducible manner in high overall yield, with low costs of production and high purity, and that meets all regulatory requirements needing to be obeyed so that the substance can be used in clinical trials and for later official filing. It would also be advantageous to isomerize the unwanted enantiomer and return the resulting racemate to the process once again.

Surprisingly, a very efficient method has now been found for producing the compound of formula (I), which meets the aforementioned requirements. The new method according to the invention (method variant (A)) furnishes the target compound (I) in 8 steps (see schemes 7, 2 and 3, below) in more than 17% of theory overall yield without a chromatographic purification of intermediates. An alternative method variant (B) (see schemes 7, 4, 5 and 6, below) of the method according to the invention furnishes the target compound (I) in 9 steps, likewise without a chromatographic purification of intermediates, with the overall yield depending on the reaction management, as described below.

The subject matter of the present invention is a method for producing compounds of formula (I)

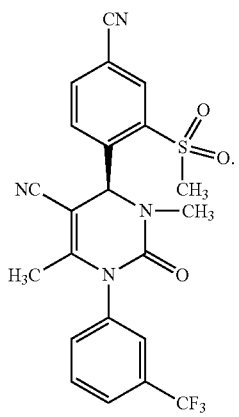

characterized in that one reacts a compound of formula (IX)

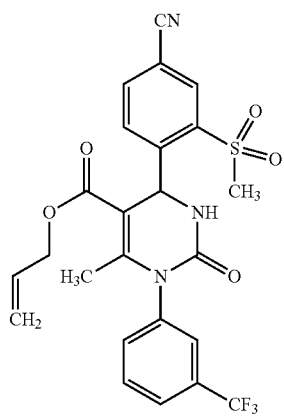

a-1) in the presence of a methylation agent and a base to form a compound of formula (XVI);

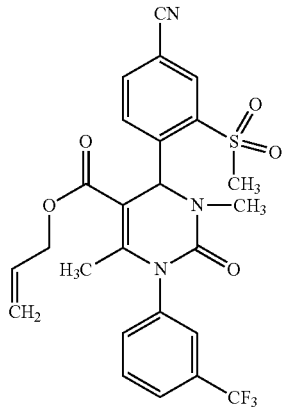

then
a-2) reacts a compound of formula (XVI) in the presence of a palladium catalyst and a secondary amine base to form a compound of formula (XXVI)

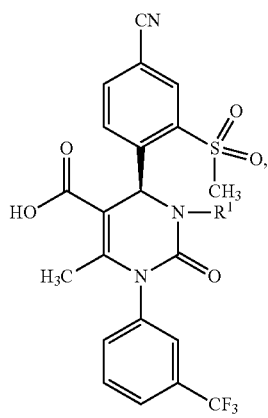

in which $R^1$ stands for methyl,
or
b-1) reacts it in the presence of a palladium catalyst and a secondary amine base to form a compound of formula (XXVI), in which $R^1$ stands for hydrogen,
then
c) reacts a compound of formula (XXVI), in which $R^1$ stands for hydrogen or methyl, in the presence of a cinchona alkaloid and a solvent to form compounds of formulas (XXVIII) and (XXIX)

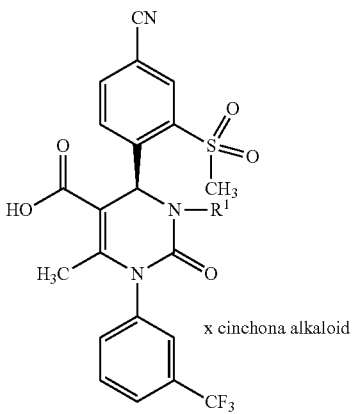

-continued

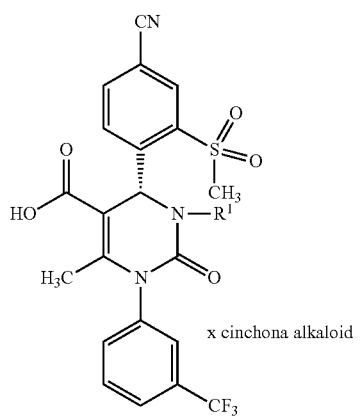
(XXIX)

x cinchona alkaloid in which R¹ in formula (XXVIII) and in formula (XXIX) stands for hydrogen or in which R¹ in formula (XXVIII) and in formula (XXIX) stands for methyl; then
d) isolates a compound of formula (XXVIII); then
e) reacts a compound of formula (XXVIII) in the presence of a strong acid to form a compound of formula (XXVII)

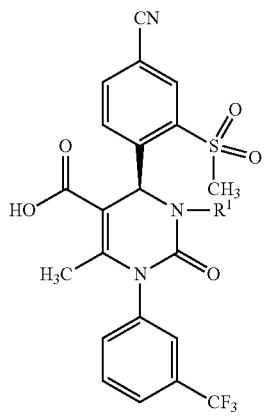
(XXVII)

in which R¹ stands for hydrogen or methyl; then
b-2) in the event that R¹ in the compound of formula (XXVII) stands for hydrogen, one reacts a compound of formula (XXVII) in the presence of an allyl halide or sulfonate and a base to form a compound of formula (X)

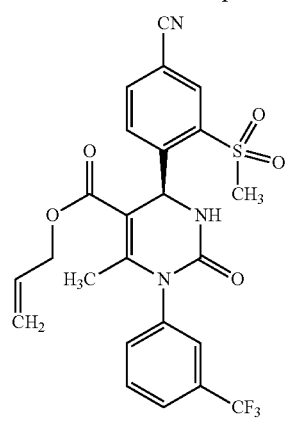
(X)

then
b-3) reacts a compound of formula (X) in the presence of a methylation agent and a base to form a compound of formula (XXIII)

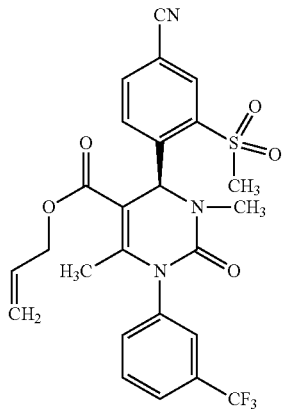
(XXIII)

then
b-4) reacts a compound of formula (XXIII) in the presence of a palladium catalyst and a base to form a compound of formula (XXVII)

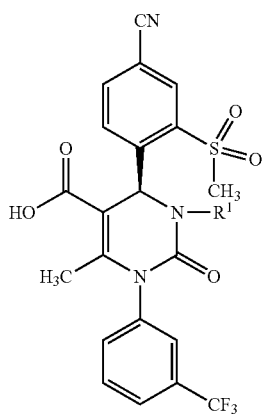
(XXVII)

in which R¹ stands for methyl; then
f) reacts a compound of formula (XXVII), in which R¹ stands for methyl, in the presence of an activation reagent, to form a compound of formula (XIX)

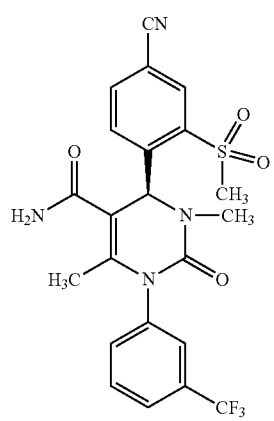
(XIX)

then g) reacts a compound of formula (XIX) in the presence of a dehydrating agent, to form a compound of formula (I);

and if necessary after reaction step c), isolates a compound of formula (XXIX)

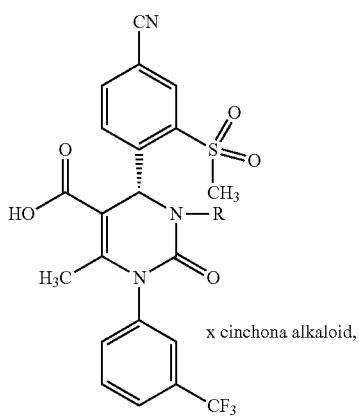

(XXIX)

x cinchona alkaloid, in which R¹ stands for hydrogen, reacts this according to step e) in the presence of a strong acid to form a compound of formula (XXX)

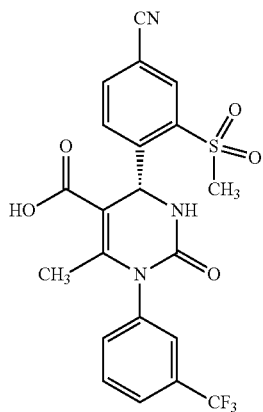

(XXX)

and then reacts a compound of formula (XXX) according to reaction step b-2) in the presence of an allyl halide or sulfonate and a base to form a compound of formula (XXXI)

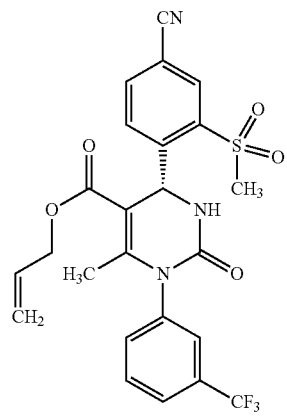

(XXXI)

then h) reacts a compound of formula (XXXI) in the presence of a strong, non-nucleophilic base in a solvent and under simultaneous heating to form the racemate of formula (IX)

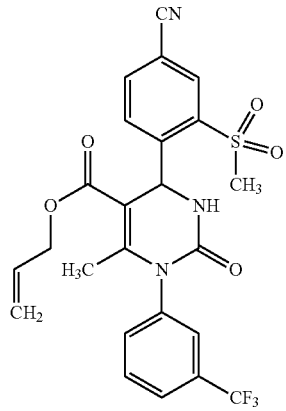

(IX)

then reacts a compound of formula (IX) according to the above-described reaction steps b-1), c), d), e), b-2), b-3), b-4), f) and g) to form a compound of formula (I);

and if necessary repeats the reaction steps of isolation of a compound of formula (XXIX), its reaction by reaction step e) in the presence of a strong acid to form a compound of formula (XXX), the subsequent reaction of a compound of formula (XXX) according to reaction step b-2) in the presence of an allyl halide or sulfonate and a base to form a compound of formula (XXXI), and then the performance of the reaction steps h), b-1), c), d), e), b-2), b-3), b-4), f) and g), one or more times.

The method according to the invention is described in two method variants. Method variant (A) comprises the above-described steps a-1), a-2), c), d), e), f) and g). The racemate splitting, a key step of the synthesis, takes place in method variant (A) at the step of the compound of formula (XXVI), in which R¹ stands for methyl. Method variant (B) comprises the above-described steps b-1), c), d), e), b-2), b-3), b-4), f) and g). The racemate splitting, a key step of the synthesis, takes place in method variant (B) at the step of the compound of formula (XXVI), in which R¹ stands for hydrogen.

According to one embodiment of the present invention, R¹ in formulas (XXVI), (XXVII), (XXVIII) and (XXIX) stands for methyl and the method comprises the above-described reaction steps a-1), a-2), c), d), e), f) and g).

According to one embodiment of the present invention, R¹ in formulas (XXVI), (XXVII), (XXVIII) and (XXIX) stands for hydrogen and the method comprises the above-described reaction steps b-1), c), d), e), b-2), b-3), b-4), f) and g).

According to one embodiment of the present invention, R¹ in formulas (XXVI), (XXVII), (XXVIII) and (XXIX) stands for hydrogen and the method comprises the above-described reaction steps b-1), c), d), e), b-2), b-3), b-4), f) and g) and after reaction step c), a compound of formula (XXIX) is isolated, this is reacted according to reaction step e) in the presence of a strong acid to form a compound of formula (XXX); then a compound of formula (XXX) is reacted according to reaction step b-2) in the presence of an allyl halide or sulfonate and a base to form a compound of formula (XXXI); then h) a compound of formula (XXXI) is reacted in the presence of a strong, non-nucleophilic base in a solvent and under simultaneous heating to form the racemate of formula (IX); then a compound of formula (IX) is reacted according to the above described reaction steps b-1), c), d), e), b-2), b-3), b-4), f) and g) to form a compound of formula (I);

and if necessary, the steps of isolation of a compound of formula (XXIX), its reaction by reaction step e) in the presence of a strong acid to form a compound of formula (XXX), the subsequent reaction of a compound of formula (XXX) according to reaction step b-2) in the presence of an allyl halide or sulfonate and a base to form a compound of formula (XXXI), and then the above described reaction steps h), b-1), c), d), e), b-2), b-3), b-4), f) and g) are repeated one or more times.

Methylation agents that can be used for the reaction steps a-1) and b-3) are, for example, methyl iodide, dimethyl sulfate, dimethyl carbonate, toluene sulfonic acid methyl ester or methane sulfonic acid methyl ester, with methyl iodide and dimethyl sulfate being preferred. Bases that can be used for the reaction steps a-1) and b-3) are, for example, sodium hydride, sodium hexamethyl disilazane and lithium hexamethyl disilazane, with sodium hexamethyl disilazane and lithium hexamethyl disilazane being preferred. As the solvent for reaction step a-1), tetrahydrofuran (THF) is used in four- to sixfold excess in terms of the weight of the compound of formula (IX). The reaction temperature is −70 to 40° C., preferably 0 to 30° C.

According to one embodiment of the present invention, the reaction steps a-1) and b-3) use 2 eq. of dimethyl sulfate ($Me_2SO_4$) as the methylation agent and sodium bis(trimethylsilyl)amide (NaHMDS) as the base.

WO 2009/080199 A1 also describes a synthesis pathway that makes it possible to introduce the methyl group as early as the allyl ester step (X). Using LiHMDS, deprotonation was carried out at a temperature of −78° C. and then the methyl group was introduced by adding 5 eq. of methyl iodide. The methylated S-allyl ester after processing and chromatographic purification was obtained in a yield of 59% (example 122). The saponification to the corresponding acid (XVIII) is likewise described (example 35A). However, no further reaction to form the end product of formula (I) via the amide (XIX) is described here.

With the goal of avoiding an alkylation with methyl iodide at the end step, according to one embodiment of the method of the invention the racemic allyl ester of formula (IX) is methylated in analogy to the synthesis described in WO 2009/080199 A1 (example 122). Unlike the synthesis described in WO 2009/080199 A1, the methylation of the allyl ester in the method of the invention occurs at the stage of the racemate. The reaction according to the invention has significant improvements as compared with the prior art. Thanks to the use of NaHMDS as the base, the reaction can be carried out at a temperature of 20° C. in a four- to sixfold excess of THF, in relation to the weight of the compound of formula (IX). This is significant for a synthesis on a large technical scale, since now no cost-intensive low-temperature reactor is required. Furthermore, the rather costly methylation agent methyl iodide can be replaced by the economical alkylation reagent dimethyl sulfate. One uses 2 eq. of dimethyl sulfate. The excess methylation agent is removed after the end of the reaction by adding aqueous ammonia solution. The product (XVI) can be isolated directly from the reaction mixture by water precipitation. After isolation, drying is carried out in a vacuum. The yields of this reaction are generally >80% of theory.

Palladium catalysts that can be used for the saponification of the allyl esters of formula (XVI), (IX) or (XXIII) according to reaction steps a-2), b-1) and b-4) are, for example, palladium-(O)-phosphane complexes such as tetrakis (triphenylphosphine) palladium(0) ($Pd(PPh_3)_4$) and palladium-acetate/triphenylphosphine ($PdOAc_2/PPh_3$), with Pd-acetate/triphenylphosphine being preferred. Secondary amine bases that can be used for the reaction step a-2) are, for example, morpholine, piperidine, diisopropyl amine and N-methyl-piperazine, with morpholine and N-methyl-piperazine being preferred. As the solvent for the reaction steps a-2), b-1) and b-4), tetrahydrofuran (THF) is used for example in three- to fivefold excess, in relation to the weight of the compound of formula (XVI), (IX) or (XXIII).

According to one embodiment of the present invention, in reaction steps a-2), b-1) and b-4) palladium acetate ($PdOAc_2$) is used as the palladium catalyst, with triphenylphosphine ($PPh_3$) as ligands and morpholine as the base.

The saponification of the racemic allyl ester (XVI) to the free acid (XVII) is carried out in reliance on the protocol as published in WO 2009/080199 A11 (example 5A, here at the stage of the S-enantiomer). The reaction according to the invention has significant improvements over the prior art.

For instance, the relatively costly and air-sensitive catalyst palladium tetrakistriphenylphosphine is replaced by the stable palladium acetate with addition of triphenylphosphine as ligand. Furthermore, the catalyst quantity can also be reduced from 0.05 eq. to 0.003 eq. The palladium-catalyzed allyl ester cleavage is carried out in a three- to fivefold excess of THF, in relation to the weight of the compound of formula (XVI), at temperatures of 40 to 60° C. in 1 to 3 h with addition of morpholine as the base. The product (XVII), which occurs as a THF-solvate, can be isolated directly from the reaction mixture by water precipitation. After the isolation, it is dried in a vacuum. The yields of this reaction are generally >95% of theory.

The splitting of the racemate mixture of the acids of formula (XXVI), where $R^1$ is hydrogen or methyl, according to reaction step c) of the present invention, is a key step in the method of the invention for producing the compound of formula (I). Cinchona alkaloids that can be used for reaction step c) (racemate splitting) are selected from the group consisting of quinine, quinidine, cincholine and cincholidine. Preferable are quinine and quinidine. Solvents that can be used for reaction step c) are, for example, aqueous alcohol systems, preferably isopropanol/water, especially preferably isopropanol/water in a ratio of 9:1. Furthermore, esters of acetic acid may be used as the solvent for reaction step c), preferably the $C_2$ to $C_5$ alkyl acetates, especially preferably n-butyl acetate.

According to one embodiment of the present invention, the cinchona alkaloid for reaction step c) is selected from the group consisting of quinine and quinidine.

According to one embodiment of the present invention, the solvent for reaction step c) is selected from $C_2$-$C_5$ alkyl esters of acetic acid, $C_1$-$C_6$ alcohols and mixtures of $C_1$-$C_6$ alcohols and water.

According to one embodiment of the present invention, for reaction step c) in the case of the reaction of a compound of formula (XXVI), in which $R^1$ stands for methyl, a combination of quinidine as the cinchona alkaloid and n-butyl acetate as the solvent is used. The diastereomeric quinidine salts of the compound of formula (XXVI), in which $R^1$ stands for methyl, may be separated from each other according to the method of the invention in solvents such as the esters of acetic acid, preferably the $C_2$ to $C_5$ substituted esters, especially preferably n-butyl acetate. For instance, the racemic compound of formula (XXVI), in which $R^1$ stands for methyl, is reacted in a 4- to 6 fold excess of butyl acetate, in relation to the weight of the compound of formula (XXVI with $R^1$=methyl), while adding 1.0 to 1.1 eq. of quinidine at 40° C. to 60° C. In this case, the diastereomeric quinidine salt of the S-acid (compound of formula (XX)) crystallizes out predominantly, while the R-form (compound of formula (XXI)) remains in solution.

For the isolation of the compound of formula (XXVIII), in which $R^1$ stands for hydrogen or methyl, in reaction step d), the solid is filtered off, washed with the solvent used in reaction step c), and dried in vacuum.

Strong acids that can be used for reaction step e) are, for example, aqueous hydrochloric acid, aqueous hydrobromic acid, and aqueous sulfuric acid.

According to one embodiment of the present invention, acidification down to pH 1 is carried out in reaction step e) with aqueous hydrochloric acid.

According to one embodiment of the present invention, in reaction step e) the diastereomer-pure quinidine salt (compound of formula (XX)) is suspended in water to release the acid. After acidification with aqueous hydrochloric acid (down to pH=1), the quinidine auxiliary base remains in solution as a hydrochloride, while the enantiomer-pure acid (compound of formula (XXVII), in which $R^1$ stands for methyl) precipitates out. After isolation, drying is carried out in vacuum. The yields of this racemate splitting and liberation to form the S-acid (compound of formula (XXVII), in which $R^1$ stands for methyl) are generally >40% of theory, with an enantiomer excess of >98%.

The other isomer can likewise be obtained from the mother liquor of the racemate splitting by concentrating and subsequent aqueous acidic processing.

According to another embodiment of the present invention, for reaction step c) in the case of the reaction of a compound of formula (XXVI), in which $R^1$ stands for hydrogen, a combination of quinine as the cinchona alkaloid and a mixture of isopropanol and water as the solvent is used. The diastereomeric quinine salts of the acid of formula (XXVI), in which $R^1$ stands for hydrogen, are separated from each other in aqueous alcoholic systems, preferably isopropanol/water, especially preferably isopropanol/water in a ratio of 9:1. According to this embodiment, the racemic acid of formula (XXVI), in which $R^1$ stands for hydrogen, is reacted in 6- to 10-fold excess of isopropanol/water, in relation to the weight of the compound of formula (XXVI), while adding 1.0 to 1.1 eq. of quinine at 40° C. to 60° C. Primarily the diastereomeric quinine salt of the S-acid (compound of formula (XXIV)) crystallizes in this process, while the R-form (compound of formula (XXV)) remains in solution.

For the isolating of the compound of formula (XXIV) according to reaction step d), the solid is filtered off, washed with isopropanol/water, and dried in vacuum.

According to step e), in order to liberate the acid of formula (XXVII), in which $R^1$ stands for hydrogen, the diastereomer-pure quinine salt (XXIV) is suspended in water. After acidification with aqueous hydrochloric acid (down to pH=1), the quinine auxiliary base remains in solution as a hydrochloride, while the enantiomer-pure acid precipitates out. After isolation, drying is carried out in vacuum. The yields of this racemate splitting and liberation to form the S-acid of formula (XXVII), in which $R^1$ stands for hydrogen, are generally >45% of theory, with an enantiomer excess of >98%. The total yield of this reaction sequence is 18%.

The other isomer can likewise be obtained from the mother liquor of the racemate splitting by concentrating and subsequent aqueous acidic processing.

The success of such a racemate splitting is highly dependent on the substance and cannot be predicted. The method according to the invention for racemate splitting as described in reaction step c) is therefore surprising.

The methylation of the compound of formula (XXVII), in which $R^1$ stands for hydrogen, cannot be carried out directly with the free carboxylic acid of formula (XXVII, $R^1$=hydrogen). Therefore, the carboxylic acid of formula (XXVII, $R^1$=hydrogen) must first be converted to a corresponding ester, preferably back to an allyl ester of formula (X). This is done by the methods basically known to the skilled person according to reaction step b-2) of the present invention by alkylation with an allyl halide or sulfonate, such as an allyl bromide, allyl chloride, allyl iodide, allyl methane sulfonate or allyl toluene sulfonate in the presence of bases such as potassium carbonate, sodium hydroxide, potassium hydroxide, sodium carbonate or sodium hydride in solvents such as acetone. In this way, the carboxylic acid (XI) can be converted in a yield of 95% into the corresponding allyl ester (X). The following steps to the target compound (I) are carried out similarly to the method described in variant (A).

According to one embodiment, allyl bromide in the presence of potassium carbonate is used for the reaction step b-2).

The formation of the amide from the acid was carried out in the synthesis according to WO 2009/080199 A1 with the assistance of the quite costly amide coupling reagent O-(7-azabenzotriazolo-1-yl)-N,N,N',N'-tetramethyluronium hexafluorophosphate (HATU). The amide could only be obtained after chromatographic purification. It is obvious that such a method cannot be realized on a large technical scale and thus there was a need for an alternative procedure.

It has been found, surprisingly, that during a reaction of the carboxylic acid of formula (XXVII, $R^1$=methyl) in THF, the amide of formula (XIX) crystallizes out of the reaction solution directly after water precipitation and can be obtained in high yield and purity. For this, in reaction step f) according to the present invention, the carboxylic acid of formula (XXVII, $R^1$=methyl) is first reacted with an activation reagent to form the imidazolide. The activation reagent may be, for example, 1,1'-carbonyl diimidazole together with ammonia or 1,1'-carbonyl diimidazole together with hexamethyl disilazane.

According to one embodiment of the present invention, the carboxylic acid of formula (XXVII, $R^1$=methyl) is first reacted with 1.2 to 1.7 eq., preferably 1.4 to 1.5 eq. of 1,1'-carbonyl diimidazole in THF at temperatures between 20-50° C. to form the imidazolide. As the preferred technique, it has been found to first stir for 1 to 2 hours at 20° C. and then to stir for an additional 2 to 3 hours at 50° C. After the end of the activation, one adds 5-20 eq., preferably 10 eq. of aqueous ammonia solution and stirs for 16-24 hours, preferably 16 hours, at room temperature. By a brief heating, the excess ammonia can be gassed out from the reaction mixture. For the processing, the reaction solution is slowly added to water. In this process, the product precipitates and can be isolated by filtration or centrifugation. This is then washed with water and dried in a vacuum at elevated temperature (30 to 100° C., preferably 40° C. to 70° C.). The yields are very high and generally amount to >90% of theory.

The formation of the nitrile from the amide was carried out in the synthesis according to WO 2009/080199 A1 by dehydrating it with 2 eq. of trifluoroacetic anhydride in THF. The nitrile could only be obtained after chromatographic purification. It is obvious that such a method cannot be realized on a large technical scale and thus there was a great need for an alternative procedure.

Suitable dehydrating agents for the dehydrating of amides to form nitriles according to reaction step g) of the method of the invention are, for example, 1-propane phosphonic acid anhydride (T3P) and trifluoroacetic acid anhydride. In particular, 1-propane phosphonic acid anhydride (T3P) has proven to work well for this reaction step. This reagent can be obtained as a 50% solution in ethyl acetate. It is significantly easier to handle than the extremely hydrolysis-sensitive trifluoroacetic anhydride. For this, the amide of formula (XIX) is first mixed with diisopropylethylamine (Hünig base) and then with 1-propane phosphonic acid anhydride (T3P). To complete the reaction, it is briefly heated under reflux. After the end of the reaction, the mixture is mixed with water and extracted. After this, the organic phase is washed with saturated sodium hydrogen carbonate solution and the organic phase containing the compound of formula (I) is separated.

Since the compound of formula (I) will be developed in the form of a tablet, there is a great demand for the isolated compound of formula (I) to be isolated in reproducible manner in a defined crystalline form, so that one can assure a reproducible bio-availability.

One embodiment of the invention is also the compound of formula (I) in crystal form (A), characterized in that the X-ray diffraction pattern of the compound shows peak maxima of the 2 theta angle at 7.5, 12.4, 15.1, 18.5, 18.7, 22.9, 24.7 and 26.5.

According to one embodiment of the invention, the method according to the invention provides the compound of formula (I) in crystal form (A), characterized in that the X-ray diffraction pattern of the compound of formula (I) shows peak maxima of the 2 theta angle at 7.5, 12.4, 15.1, 18.5, 18.7, 22.9, 24.7 and 26.5.

One embodiment of the invention is also the compound of formula (I) in the crystal form (A), characterized in that the Raman spectrum of the compound shows band maxima at 3075, 2928, 2918, 2236, 2216, 1646, 1605, 1195 and 1004 $cm^{-1}$.

According to one embodiment of the invention, the method according to the invention provides the compound of formula (I) in the crystal form (A), characterized in that the Raman spectrum of the compound shows band maxima at 3075, 2928, 2918, 2236, 2216, 1646, 1605, 1195 and 1004 $cm^{-1}$.

One embodiment of the invention is a method for producing the compound of formula (I) in the crystal form (A), characterized in that a compound of formula (I), present in one or more crystal forms or as a solvate, is crystallized out in an alcohol, preferably ethanol, after which the resulting crystal paste is heated to 50-80° C. and further stirred for 2-5 h at this temperature. One embodiment of the invention is the compound of formula (I) in crystal form (A) for treatment of illnesses.

One embodiment of the invention is the compound of formula (I) in crystal form (A) for use in a method for treatment and/or prevention of diseases of the lungs and the cardiovascular system and for promoting wound healing, especially for chronic wounds.

One embodiment of the invention is the compound of formula (I) in crystal form (A) for use in a method for treatment and/or prevention of pulmonary arterial hypertonia (PAH) and other forms of pulmonary hypertonia (PH), of chronic obstructive lung diseases (COPD), of acute lung injury (ALI), of acute respiratory disease syndrome (ARDS), of pulmonary emphysema, of alpha-1-antitrypsin deficiency (AATD), of cystic fibrosis (CF), of bronchiectasis and to promote wound healing, especially chronic wounds.

One embodiment of the invention is a pharmaceutical containing the compound of formula (I) in crystal form (A) in more than 90 wt. percent in relation to the total quantity of the contained compound of formula (I).

One embodiment of the invention is the use of the compound of formula (I) in crystal form (A) for producing a pharmaceutical for treatment of diseases of the lungs and the cardiovascular system and for promoting wound healing, especially for chronic wounds.

One embodiment of the invention is a method for the treatment of diseases of the lungs and the cardiovascular system and for the promoting of wound healing, especially for chronic wounds, by administering an effective quantity of the compound of formula (I) in crystal form (A).

Another embodiment of the invention is a method for producing a compound of formula (I) in crystal form (A), characterized in that one produces a compound of formula (I) according to the method of the invention, crystallizes the compound of formula (I) from the organic phase from reaction step g) of the method of the invention in an alcohol, preferably ethanol, and then heats the resulting crystal paste to 50-80° C. and stirs this for another 2-5 h at this temperature.

For the final crystallization method, for GMP-technical reasons the product solution in ethyl ester is at first subjected to a particle filtration and then reacted at reflux temperature (60° C.-80° C.) with ethanol, preferably using ethanol denatured with toluene. Under continued addition of ethanol (toluene-denatured), the ethyl ester is distilled off. The compound of formula (I) crystallizes out. In order to ensure a better filtering ability, the crystal paste is heated to 60° C.-80° C. and stirred for another 4 h at this temperature. This is cooled to 20° C., and then the crystals are isolated and dried in a vacuum at 40-50° C. The yields are generally >80% of theory. The achieved chemical purity of >99.2% and the content of around 100% meet the criteria for commercial products according to the ICH Guidelines. The quantity of residual solvent, in this case ethanol, is <0.1%. The optical purity is >>99% e.e.

The crystallization method is very robust and furnishes the desired crystal form (A) in a reproducible manner (melting point 232° C.). The compound of formula (I) is generally micronized and formulated into tablets at the pharmacy. It has been found that the crystal form (A) possesses very good stability properties, even at high humidity, and can be stored for more than 3 years with no loss of stability.

As described above, the NH-allyl ester of formula (XXXI) can be produced by isolation of a compound of formula (XXIX), its reaction according to reaction step e) in the presence of a strong acid to form a compound of formula (XXX) and then the reaction of a compound of formula (XXX) according to reaction step b-2) in the presence of an allyl halide or sulfonate and a base. It has been discovered surprisingly that this NH-allyl ester of formula (XXXI) can be racemized. It is thus possible to transform the unwanted enantiomer, which accrues in large quantities, back to the racemic form and thus return it to the process. For this, the carboxylic acid obtained from the mother liquors of the racemate splitting, containing primarily R, is first converted into an allyl ester under the above-described conditions similar to step b-2) according to the invention. By treatment with strong, non-nucleophilic bases, such as 1,8-diazabicyclo[5.4.0]undec-7-ene (DBU) in solvents, such as THF, the primarily R-containing mixture can be racemized almost completely by heating under reflux for several hours. After adding the reaction mixture to water, the racemic allyl ester of formula (IX) precipitates out, is isolated and dried. The allyl ester of formula (IX) is then saponified once more under the above-described conditions according to reaction step b-1) to form the acid of formula (XXVI, R¹=hydrogen). With this method, it was possible to recover 40% of the quantity of acid of formula (XXVI, R¹=hydrogen) that was used for the racemate splitting. With a recovery cycle, it was possible to boost the total yield of the reaction sequence from an original 18%0 to 25%.

Another embodiment of the present invention is a method for producing a compound of formula (XXVII)

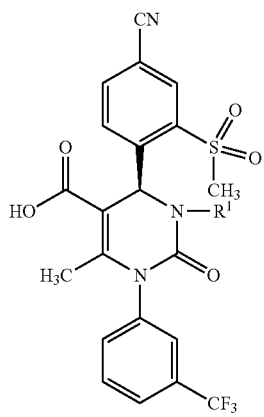
(XXVII)

characterized in that one
c) reacts a compound of formula (XXVI)

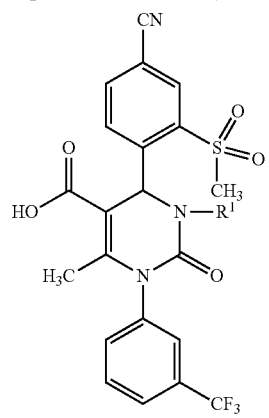
(XXVI)

in the presence of a cinchona alkaloid and a solvent to form compounds of formulas (XXVIII) and (XXIX)

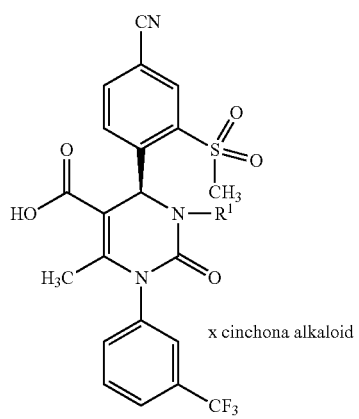
(XXVIII)

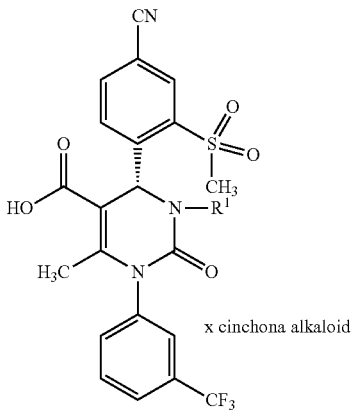
(XXIX)

d) then isolates a compound of formula (XXVIII); then
e) reacts a compound of formula (XXVIII) in the presence of a strong acid to form a compound of formula (XXVII), where R¹ in the compounds of formulas (XXVI), (XXVII), (XXVIII) and (XXIX) stands for hydrogen or methyl.
The reaction conditions for this reaction sequence are as described above.

Another embodiment of the present invention is a method for producing a compound of formula

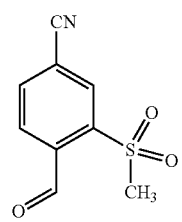
(VI)

characterized in that one reacts a compound of formula (XV)

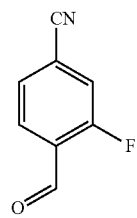
(XV)

in the presence of NaSO₂Me and DMSO or sulfolane at 40-60° C. to form a compound of formula (VI).

According to one embodiment of the present invention, the reaction of the compound of formula (XV) to form the compound of formula (VI) is carried out in a three- to fivefold excess of DMSO or sulfolane, in relation to the weight of the compound of formula (XV).

One advantage of this high concentration of the compound of formula (XV) in the reaction batch is an increased economy of the method.

As the starting material for 4-formyl-3-(methylsulfonyl) benzonitrile of formula (VI), 4-bromo-2-fluorobenzaldehyde of formula (XIV) is used, which is first converted into 3-fluoro-4-formylbenzonitrile of formula (XV) in known manner by methods familiar to the skilled person (Synth. Commun. 1994, 887-890, Angew. Chemie 2003, 1700-1703, Tetrahedron Lett. 2007, 2555-2557, Tetrahedron Lett. 2004, 1441-1444, JACS 2003, 125, 2890-2891, Journal of Organometallic Chemistry 689 (2004), 4576-4583). It has proven to be especially advantageous to carry out a palladium-catalyzed reaction with potassium hexacyanoferrate*3H$_2$O as the cyanide source (Tetrahedron Lett. 48 (2007), 1087-1090). For this, 4-bromo-2-fluorobenzaldehyde (XIV) is placed in DMF (4-6-fold excess in relation to the weight of the compound of formula (XIV)), 0.22 eq. of potassium hexacyanoferrate*3H2O and 1 eq. of sodium hydrogen carbonate are provided and then 0.005 eq. of palladium acetate are added. This is heated for 3 hours at 120° C. The solution is cooled down to 20° C., then water and MtBE are added. The organic phase is separated, the aqueous phase is again washed with MtBE and then the combined MtBE phases are concentrated while adding water. The product precipitates out. After isolation, the product is dried in a vacuum. The yields of this reaction are generally >75% of theory. In the meantime, 3-fluoro-4-formylbenzonitrile (XV) has also become commercially available.

The introduction of a methylsulfonyl group into a 2-fluoro-substituted benzaldehyde has been described for example in WO 2004/52858 (ELI LILLY). The reaction of 2-fluorobenzaldehyde with sodium methane sulfinate in DMSO at 100° C. in 16 h furnished the desired product, but only in a 50% yield. Surprisingly, it has been discovered that 3-fluoro-4-formylbenzonitrile (XV) is converted entirely to the desired 4-formyl-3-(methylsulfonyl)benzonitrile (VI) even under relatively mild reaction conditions (40-60° C., preferably 50° C., 4 h) in a 3- to 5-fold excess of DMSO, in relation to the weight of the compound of formula (XV), by reaction with sodium methane sulfinate. It was possible to isolate the product directly from the reaction mixture by water precipitation. After the isolation, the product is dried in a vacuum. The yields of this reaction are generally >90% of theory.

Thus, a very efficient approach has been found for the intermediate 4-formyl-3-(methylsulfonyl)benzonitrile (VI).

It was possible to produce the condensation product of the Biginelli reaction, (rac)-allyl 4-(4-cyano-2-(methylsulfonyl) phenyl)-6-methyl-2-oxo-1-[3-(trifluoromethyl)phenyl]-1,2,3,4-tetrahydropyrimidine-5-carboxylate (IX) from 4-formyl-3-(methylsulfonyl)benzonitrile (VI), 1-[3-(trifluoromethyl)phenyl]urea (VII) and allyl-3-oxobutanoate (VIII) in reliance on the synthesis protocol as published in WO 2009/080199 A1. Here as well, it was possible to significantly boost the yield from 64% to 87%.

The subject matter of the present invention is also compounds of formula (XXVII)

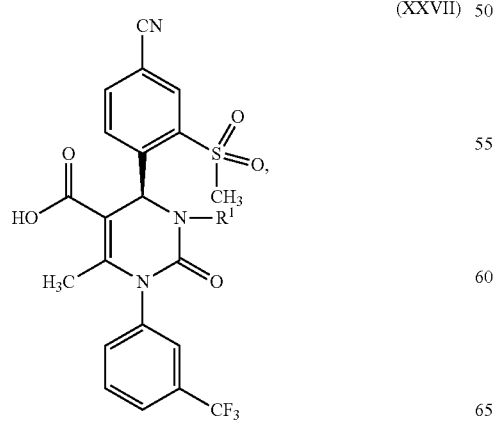

(XXVII)

in which R$^1$ stands for hydrogen or methyl, as well as its salts and solvates.

The following scheme 2 shows in detail the intermediate stages of method variant (A).

Scheme 2

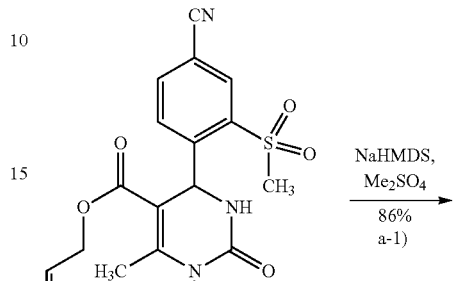

(IX)

NaHMDS, Me$_2$SO$_4$
→
86%
a-1)

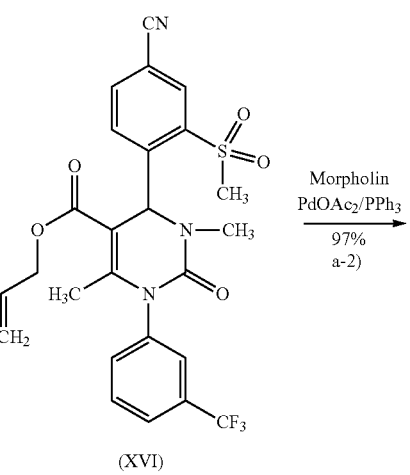

(XVI)

Morpholin PdOAc$_2$/PPh$_3$
→
97%
a-2)

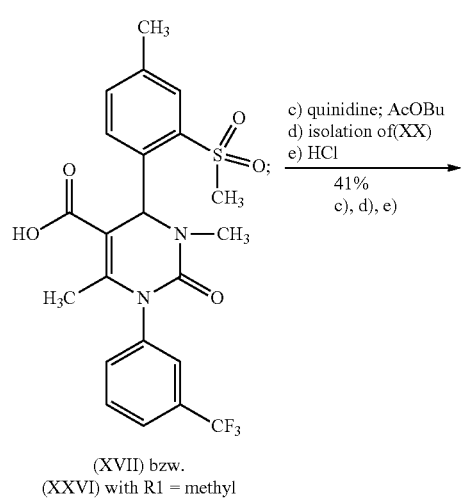

(XVII) bzw.
(XXVI) with R1 = methyl c) quinidine; AcOBu
d) isolation of (XX)
e) HCl
→
41%
c), d), e)

According to one embodiment of the present invention, the steps shown in the following scheme 3 are performed during the racemate splitting in the context of method variant (A).
Scheme 3
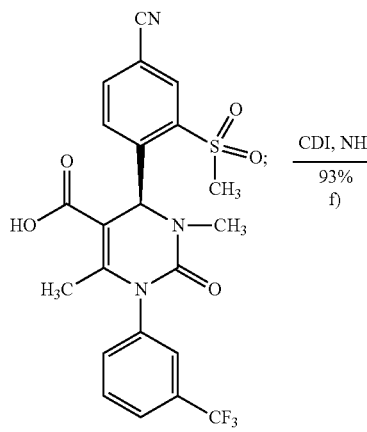
(XVIII) bzw.
(XXVII) with R1 = methyl
CDI, NH₃
93%
f)
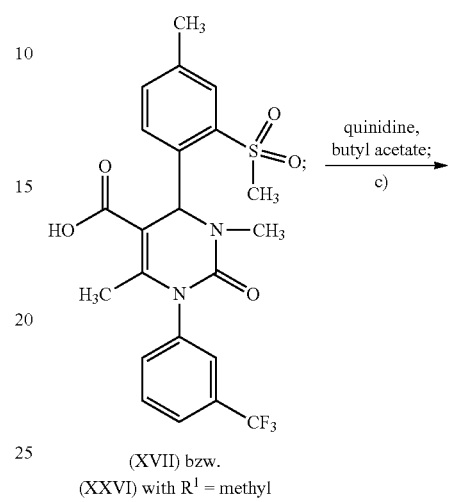
(XVII) bzw.
(XXVI) with R¹ = methyl
quinidine,
butyl acetate;
c)
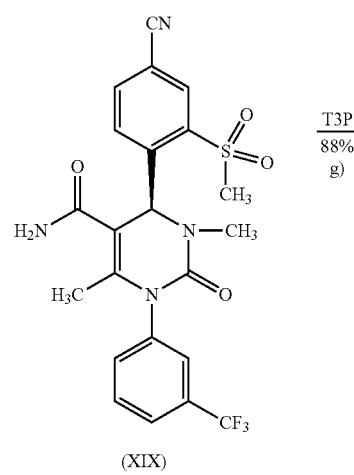
(XIX)
T3P
88%
g)
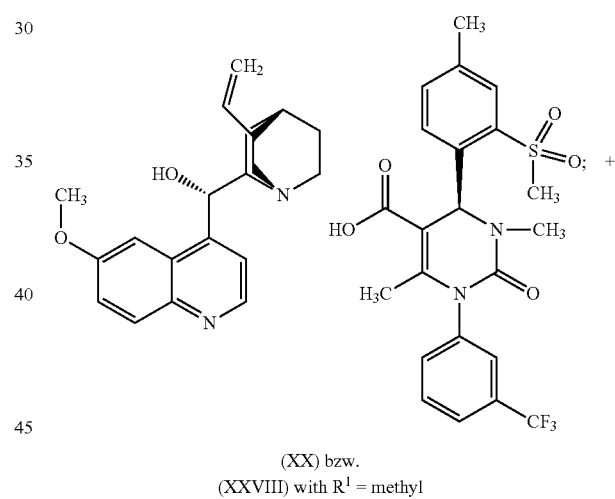
(XX) bzw.
(XXVIII) with R¹ = methyl
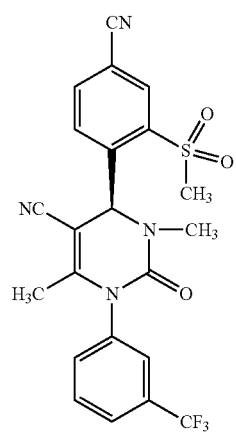
(I)
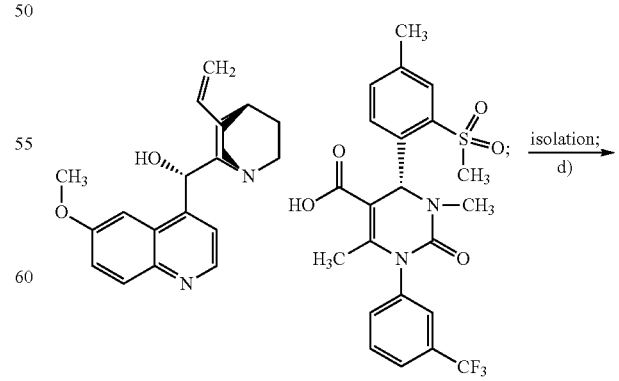
(XXI) bzw.
(XXIX) with R¹ = methyl
isolation;
d)

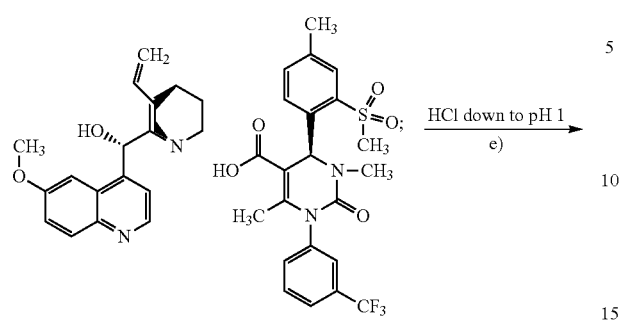
(XX) bzw.
(XXVIII) with R¹ = methyl
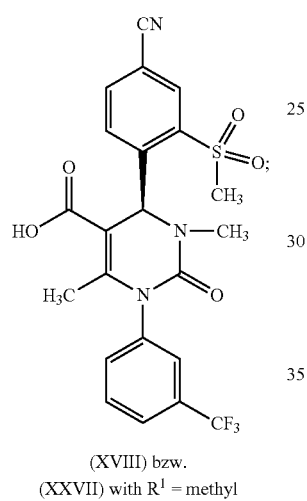
(XVIII) bzw.
(XXVII) with R¹ = methyl
The following scheme 4 shows in detail the intermediate steps of method variant (B)
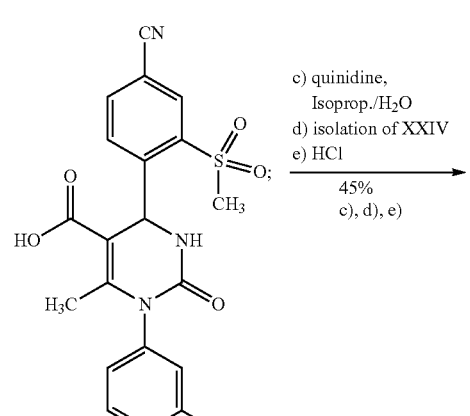
(XVII) bzw.
(XXVI) with R¹ = H
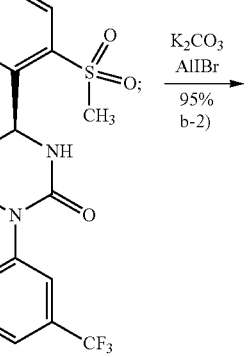
(XI) bzw.
(XXVII) with R¹ = H
Scheme 4
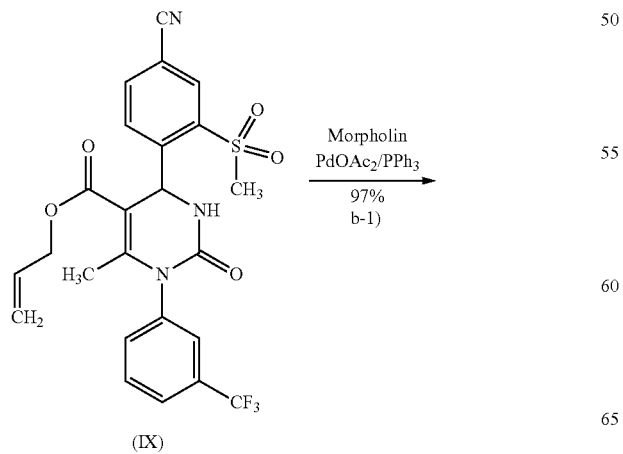
(IX)
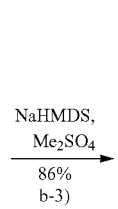
(X)

According to one embodiment of the present invention, the steps shown in the following scheme 5 are performed during the racemate splitting in the context of method variant (B).
Scheme 5
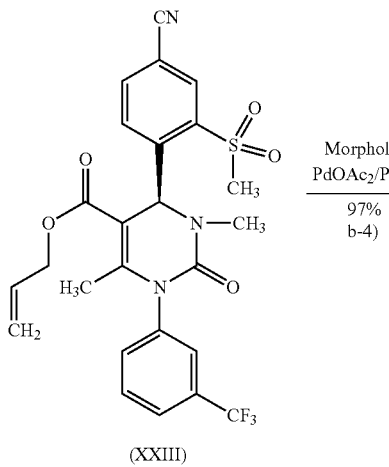
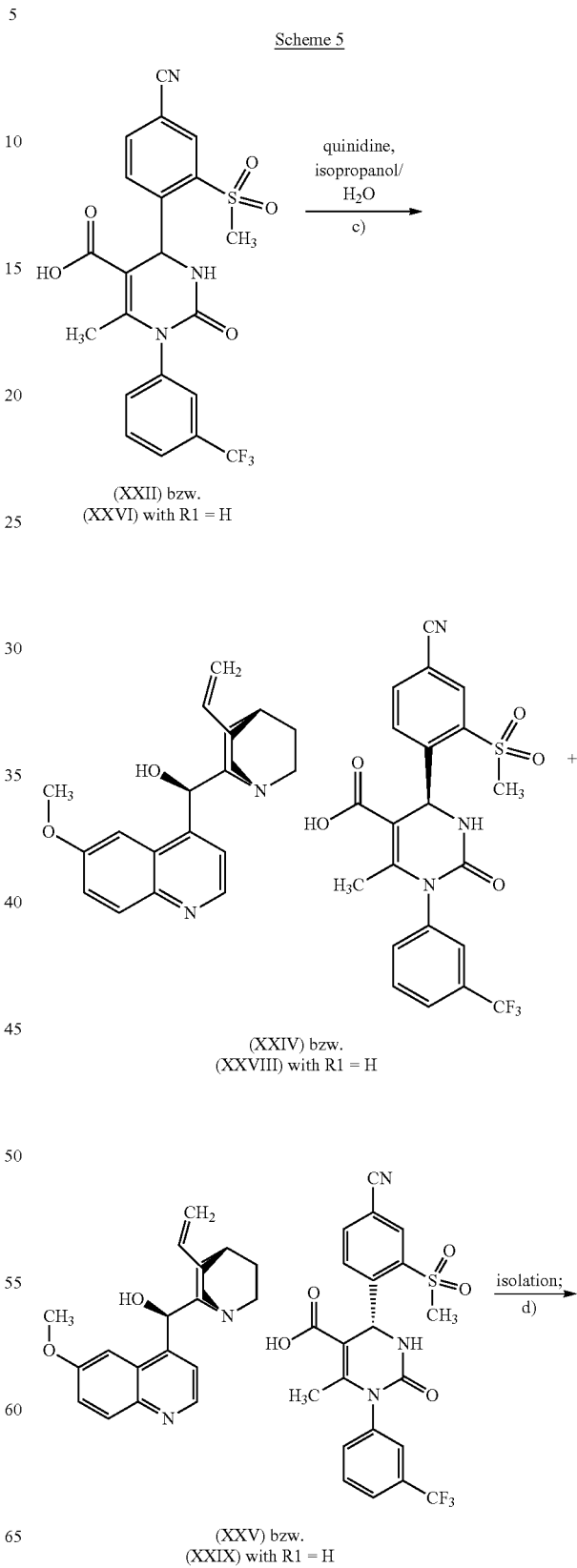

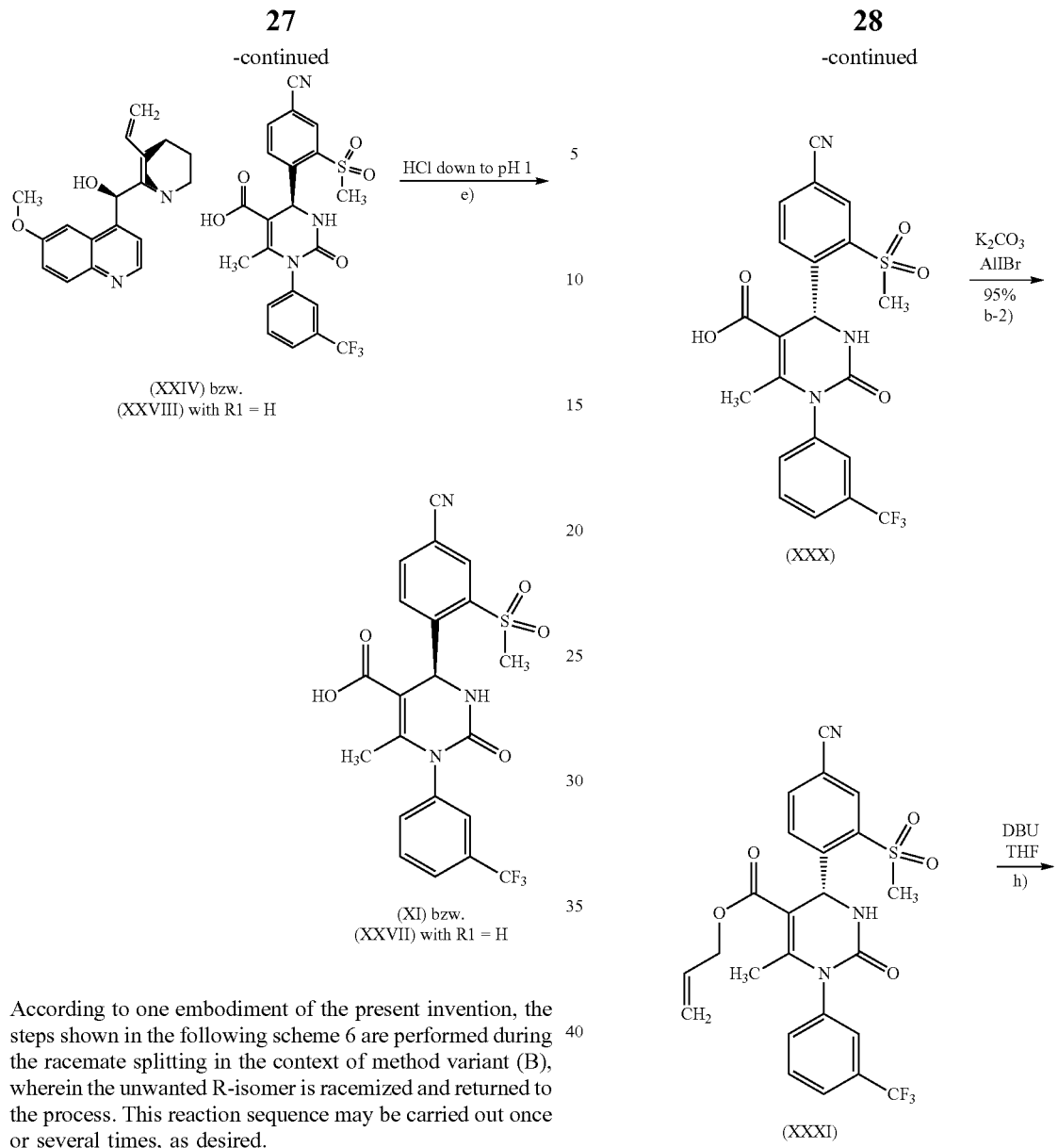
According to one embodiment of the present invention, the steps shown in the following scheme 6 are performed during the racemate splitting in the context of method variant (B), wherein the unwanted R-isomer is racemized and returned to the process. This reaction sequence may be carried out once or several times, as desired.
Scheme 6
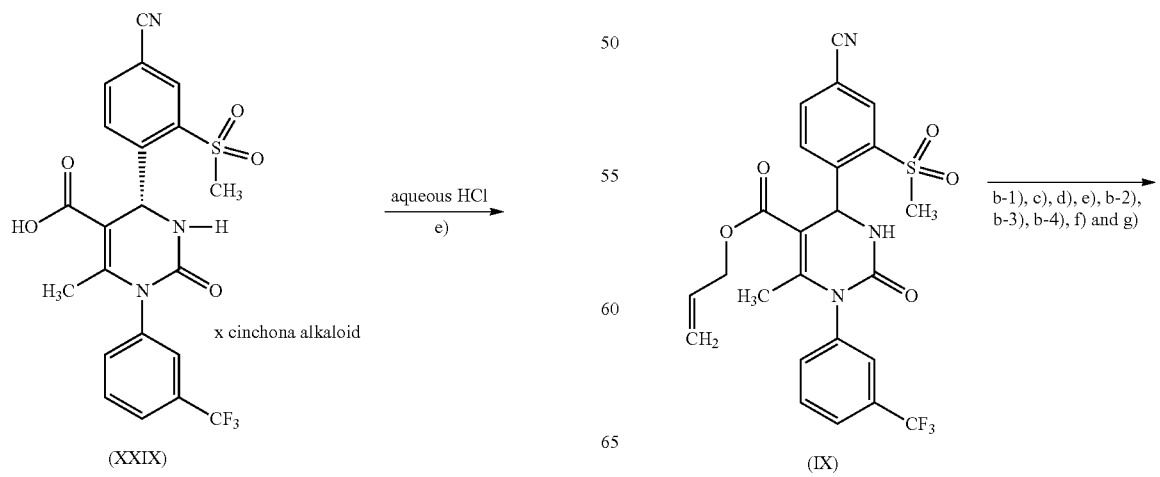

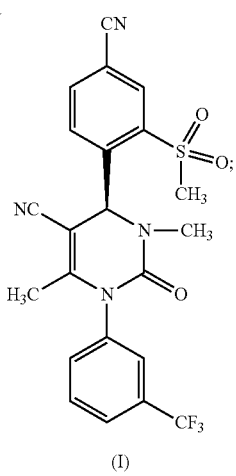

The reaction sequence for the synthesis of 4-bromo-2-fluorobenzaldehyde of formula (XIV) to form the compound of formula (IX) is represented in the following scheme 7:

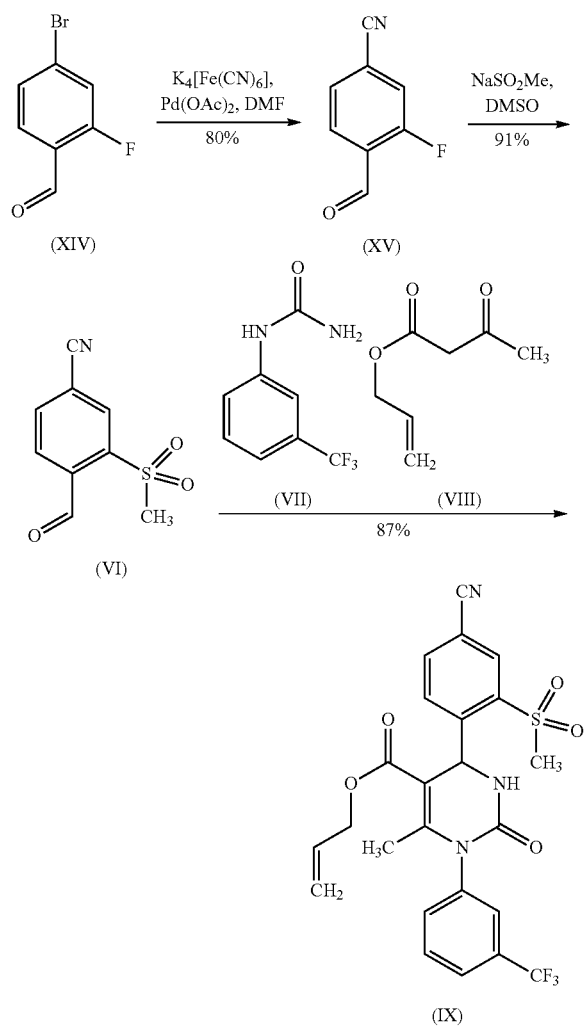

With the new synthesis according to the invention it is possible to produce the target compound (I) in a highly efficient manner. The method affords substantial advantages over the prior art, in terms of scalability and technical procedure. The overall yield is significantly higher than published data, and moreover a very high purity of the active substance is achieved. The new method enables the reproducible, economical preparation of the defined crystal form (A), not previously described in the prior art. With the method of the invention presented here, several kg of material have already been produced successfully for clinical trials.

Abbreviations

AllBr allyl bromide
aq. aqueous, aqueous solution
c concentration
cat. catalytically
CDI N,N'-carbonyl diimidazole
DBU 1,8-diazabicyclo[5.4.0]undec-7-ene
DCI direct chemical ionization (during MS)
dest. distilled
DIEA N,N-diisopropyl ethyl amine
DMAP 4-N,N-dimethylaminopyridine
DMF dimethylformamide
DMSO dimethyl sulfoxide
d. Th. of theory (for yield)
ee enantiomer excess
ent enantiomer-pure, enantiomer
eq. equivalent(s)
ESI electrospray ionization (during MS)
Et ethyl
GC-MS gas chromatography-coupled mass spectrometry
h hour(s)
HATU O-(7-azabenzotriazolo-1-yl)-N,N,N',N'-tetramethyluronium hexafluorophosphate
HPLC high-pressure, high-performance liquid chromatography
konz. concentrated
LC-MS liquid chromatography-coupled mass spectrometry
Me methyl
min minute(s)
MS mass spectrometry
MTBE methyl-tert.-butyl ether
NaHMDS sodium-bis(trimethylsilyl)amide
NMR nuclear magnetic resonance spectrometry
Ph phenyl
quant. quantitative (for yield)
rac racemic, racemate
RT room temperature
Rt retention time (in HPLC)
Schmp. melting point
TFAA trifluoroacetic acid anhydride
THF tetrahydrofuran
T3P 1-propane phosphonic acid anhydride
UV ultraviolet spectrometry
v/v volume to volume ratio (of a solution)

EXEMPLARY EMBODIMENTS

Example 1 4-formyl-3-fluorobenzonitrile (XV)

400 g (1.97 mol) of 4-bromo-2-fluorobenzaldehyde (XIV) as a solution in 2.0 l of DMF was combined with 183 g (0.433 mol) of potassium hexacyanoferrate ($K_4[Fe(CN)_6]$) and 165.5 g (1.97 mol) of sodium hydrogen carbonate, and 2.2 g (9.85 mmol) of palladium acetate was added. The result was stirred for 2.5 hours at 120° C. This was allowed to cool to 20° C. and then 2.0 l of water was added to the batch. Extraction was performed with 4.0 l of MtBE and the aqueous phase was again washed with 1.5 l of MtBE. The organic phases were combined and mixed with 2 l of water. The MtBE was for the most part distilled off at 30° C. in a slight vacuum. The product crystallized out. It was cooled down to 3° C. and stirred for one hour at this temperature. The product was filtered off and again washed with water (two times, 0.8 leach). Drying was performed at 40° C. in vacuum. Yield: 241 g (800/% of theory) of a beige-colored solid.

MS (EIpos): m/z=150 [M+H]+

1H-NMR (400 MHz, DMSO-d6): δ=7.87 (d, 1H), 7.01 (s, 1H), 8.10 (d, 1H), 10.25 (s, 1H).

Example 2 4-formyl-3-methylsulfonylbenzonitrile (VI)

200 g (1.34 mol) of 4-formyl-2-fluorobenzonitrile (XV) was provided as a solution in 0.8 l of DMSO, and 192 g (1.88 mol) of the sodium salt of methane sulfinic acid was added. This was stirred for 4 hours at 50° C. The result was allowed to cool to 20° C. The reaction mixture was added to 8.0 l of water. The product crystallized out. This was stirred for one hour at room temperature. The product was filtered off and washed with water (2 times, 0.1 l each). Drying was carried out at 40° C. in vacuum. Yield: 256 g (91% of theory) of a beige-colored solid.

MS (ESIpos): mz (%)=191.1 (15) [M-18]+, 161.0 (100).

1H-NMR (400 MHz, DMSO-d6): δ=3.57 (s, 3H), 8.10 (d, 1H), 8.38 (d, 1H), 8.45 (s, 1H), 10.62 (s, 1H).

Example 3

(rac)-4-[4-cyano-2-(methylsulfonyl)phenyl]-6-methyl-2-oxo-1-[3-trifluoromethyl)phenyl]-1,2,3,4-tetra-hydropyrimidine-5-carboxylic Acid Allyl Ester (IX)

To phosphoric acid triethyl ester (124.3 g, 683 mmol) there was added diphosphorus pentoxide (64.6 g, 455 mmol) in 3 portions at 20° C., and the result was stirred for 3 h at 40° C. This was then diluted with THF (115 ml), stirred for 30 min at 20° C., and 4-formyl-3-(methylsulfonyl)benzonitrile (VI) (119 g, 569 mmol) and 1-[3-(trifluoromethyl)phenyl]urea (VII) (116 g, 569 mmol) were added. After this, allyl acetoacetate (VIII) (121 g, 852 mmol) was apportioned for 20 min, whereupon the temperature increased to around 60° C. The mixture was stirred for 4 h at 80° C. For the processing, water (115 ml) was added at 40° C. and this was stirred for 30 min at 25° C. The product was filtered off and washed with water (280 ml). The residue was stirred with MtBE (280 ml) for 20 min, again filtered off and washed with MtBE (220 ml). Drying was carried out at 40° C. in vacuum. Yield: 259 g (87% of theory) of a beige-colored solid.

MS (ESIpos): m/z (%)=520.2 (100) [M+H]+

$^1$H-NMR (400 MHz, DMSO-d$_6$): δ=2.15 (s, 3H), 3.45 (s, 3H), 4.45 (m, 2H), 4.95 (d, 1H), 5.05 (d, 1H), 5.65 (m, 1H), 6.40 (d, 1H), 7.20 (d, 1H), 7.70 (m, 2H), 7.80 (m, 1H), 7.85 (br. s, 1H), 8.10 (br. d, 1H), 8.25 (d, 1H), 8.35 (s, 1H).

Example 4

(rac)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic Acid Allyl Ester (XVI)

(rac)-4-[4-cyano-2-(methyl sulfonyl)phenyl]-6-methyl-2-oxo-1-[3-(trifluoromethyl)phenyl]-1,2,3,4-tetra-hydropyrimidine-5-carboxylic acid allyl ester (IX) (500 g, 0.962 mol) was prepared at 20° C. in THF (2.5 l) and combined with a 1 M solution of sodium hexamethyldisilazide (NaHMDS) in THF (203 g; 1.107 mol). After 10 min of stirring, dimethyl sulfate (243 g; 1.925 mol) was added and the mixture was stirred for 2 h at RT. The reaction mixture was added to a solution of 26% aqueous ammonia solution (315 g; 4.812 mol) in 3 l of water and rinsed with 250 ml of THF. This was stirred overnight, then cooled to 5° C. The product was filtered off and washed with water (1 l). Drying was carried out at 40° C. in vacuum.

Yield: 443 g (86% of theory) of a beige-colored solid.

MS (ESIpos): m/z (%)=534.1 (100) [M+H]+; MS (ESIneg): m/z (%)=532.1 (100) [M−H]⁻.

$^1$H-NMR (400 MHz, DMSO-d$_6$): δ=2.05 (s, 3H), 2.79 (s, 3H), 3.51 (s, 3H), 4.55 (m, 2H), 5.03 (d, 1H), 5.12 (d, 1H), 5.72 (m, 1H), 6.80 (s, 1H), 7.70 (m, 2H), 7.80 (m, 1H), 7.95 (br. s, 1H), 8.15 (br. d, 1H), 8.25 (d, 1H), 8.52 (s, 1H).

Example 5

(rac)-4-[4-cyano-2-(methyl sulfonyl)phenyl]-3,6-dimethyl-2-oxo-1-[3-(trifluoromethyl)phenyl]-1,2,3,4-tetrahydropyrimidine-5-carboxylic Acid THF Solvate (XXVI)

(rac)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic acid allyl ester (XVI) (485.6 g, 0.910 mol) was prepared at 20° C. in THF (2.275 l) and combined with morpholine (118.9 g; 1.365 mol). Nitrogen was conducted into the reaction mixture for 1 h. The mixture was then heated to 50° C., combined with palladium(II) acetate (511 mg; 2.275 mmol) and triphenylphosphine (2388 mg; 9.102 mmol) and stirred for 2 h at 50° C. After cooling, the reaction mixture was placed in 4.5 l of water. 2 N hydrochloric acid was used to adjust to pH=2 and the resulting crystallizate was stirred overnight. The product was filtered off and washed with water (1.8 l). Drying was carried out at 40° C. in vacuum. Yield: 504 g (98% of theory, in relation to the mono-THF solvate) of a beige-colored solid.

MS (ESIpos): m/z (%)=494.0 (100) [M+H]⁺.

$^1$H-NMR (400 MHz, DMSO-d$_6$): δ=1.76 (m, 4H; THF), 2.08 (s, 3H), 2.77 (s, 3H), 3.48 (s, 3H), 3.60 (m, 4H, THF), 6.72 (s, 1H), 7.75 (m, 2H), 7.82 (m, 1H), 7.92 (br. s, 1H), 8.11 (br. d, 1H), 8.27 (d, 1H), 8.46 (s, 1H), 12.75 (br. s, 1H).

Example 6

(S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic Acid Quinidine Salt (XXVIII)

(rac)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic acid THF solvate (XXVI) (555 g, 0.910 mol) was prepared at 20° C. in butyl acetate (2.22 L) and combined with (+)-quinidine (334.3 g; 1.03 mol). This was then heated to 50° C. and stirred for 1 h at 50° C. After cooling to 5° C., filtering was performed, and the filter cake was stirred with butyl acetate (1.2 l), filtered again, and washed with butyl acetate (0.7 L). Drying was carried out at 40° C. in vacuum. Yield: 361 g (45% of theory) of a cream-colored solid.

$^1$H-NMR (400 MHz, DMSO-$d_6$): δ=1.58 (m, 2H), 1.79 (m, 1H), 2.04 (m, 1H), 2.07 (s, 3H), 2.33 (m, 1H), 2.77 (s, 3H), 2.79 (m, 1H), 2.90 (m, 2H), 3.21 (m, 1H), 3.33 (m, 2H), 3.51 (s, 3H), 3.90 (s, 3H), 5.11 (d, 1H), 5.14 (d, 1H), 5.53 (br. s, 1H), 6.09 (ddd, 1H), 6.72 (s, 1H), 7.75 (m, 2H), 7.82 (m, 1H), 7.92 (br. s, 1H), 8.11 (br. d, 1H), 8.27 (d, 1H), 8.46 (s, 1H), 12.75 (br. s, 1H).

Example 7

(S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic Acid (XXVII)

The quinidine salt of (S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic acid (XXVIII) (360 g, 0.405 mol) was suspended at 60° C. in a mixture of water (3.9 l) and isopropanol (0.4 l) and adjusted with 2 N of hydrochloric acid to pH=1 and stirred for 1 h at 60° C. After cooling to 20° C., the result was filtered, washed with water (0.6 l) and the filter cake was stirred with water (1.2 l), filtered again, and washed with water (1.2 l). Drying was carried out at 40° C. in vacuum. Yield: 196 g (92% of theory) of a cream-colored solid.

MS (ESIpos): m/z (%)=494.0 (100) [M+H]$^+$.

$^1$H-NMR (400 MHz, DMSO-$d_6$): δ=2.08 (s, 3H), 2.77 (s, 3H), 3.48 (s, 3H), 6.72 (s, 1H), 7.75 (m, 2H), 7.82 (m, 1H), 7.92 (br. s, 1H), 8.11 (br. d, 1H), 8.27 (d, 1H), 8.46 (s, 1H), 12.75 (br. s, 1H).

Example 8

(S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbamide (XIX)

(S)-4-[4-cyano-2-(methyl sulfonyl)phenyl]-3,6-dimethyl-2-oxo-1-[3-(trifluoromethyl)phenyl]-1,2,3,4-tetrahydropyrimidine-5-carboxylic acid (XXVII) (390.5 g, 0.791 mol) was dissolved in THF (3.9 l). To remove residual traces of water, 2 l of THF was distilled off at 80° C. bath temperature. This was combined with 1,1-carbonyldiimidazole (192.5 g, 1.187 mol) at 0° C. and stirred for 1 h at 20° C. and for 2 h at 50° C. A 26% aqueous ammonia solution (518 g, 7.91 mol) was then apportioned at 25° C. and the result was stirred for 16 h. The reaction mixture was heated to 50° C. for 2 h, and excess ammonia was gassed out. After cooling, the reaction mixture was slowly added to 7.8 l of water and the resulting crystallizate was stirred overnight. The product was filtered off and washed with water (2.4 l). Drying was carried out at 40° C. in vacuum. Yield: 361 g (92% of theory) of a cream-colored solid.

MS (ESIpos): m/z (%)=493.0 (100) [M+H]$^+$.

$^1$H-NMR (400 MHz, DMSO-$d_6$): δ=1.73 (s, 3H), 2.73 (s, 3H), 3.45 (s, 3H), 6.55 (s, 1H), 7.34 (br. s, 1H), 7.48 (br. s, 1H), 7.73 (m, 2H), 7.80 (m, 2H), 8.11 (d, 1H), 8.43 (d, 1), 8.47 (s, 1H).

Example 9

(S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile (I)

(S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbamide (XIX) (400 g, 0.812 mol) was dissolved in ethyl acetate (1.6 l). This was combined with N-ethyldiisopropylamine (262.4 g, 2.031 mol) at 20° C. and stirred for 15 min at 20° C. A 50% solution of 1-propane phosphonic acid anhydride in ethyl acetate (1.137 kg, 1.79 mol) was then apportioned at 2° C., 26%0, heated under reflux, and stirred for 2 h. This was allowed to cool to 20° C. and 3.4 l of water were added to the batch. After phase separation, the organic phase was washed with saturated sodium hydrogen carbonate solution (1.2 l). The organic phase was heated to 60° C. and distilled off in a slight vacuum while at the same time adding ethanol (toluene denatured). The product crystallizes out. When crystallization was finished, the result was heated under reflux and stirred for 4 h. This was cooled to 20° C. and stirred at this temperature for one hour. The product was filtered off and washed once with water (1.2 l) and once with ethanol (toluene denatured) (0.4 l). Drying was carried out at 50° C. in vacuum. Yield: 344 g (89%0 of theory) white crystals of the stable crystal form (A) with a melting point of 232° C., purity: 99.4%, content: 99.3%

MS (ESIpos): m/z (%)=475.1 (100) [M+H]$^+$.

$^1$H-NMR (400 MHz, DMSO-$d_6$): δ=1.81 (s, 3H), 2.70 (s, 3H), 3.52 (s, 3H), 6.48 (s, 1H), 7.65-8.40 (m, 6H), 8.46 (s, 1H).

Example 10

(rac)-4-[4-cyano-2-(methylsulfonyl)phenyl]-6-methyl-2-oxo-1-[3-trifluoromethyl)phenyl]-1,2,3,4-tetra-hydropyrimidine-5-carboxylic Acid (XXII)

(rac)-4-[4-cyano-2-(methylsulfonyl)phenyl]-6-methyl-2-oxo-1-[3-trifluoromethyl)phenyl]-1,2,3,4-tetra-hydropyrimidine-5-carboxylic acid allyl ester (IX) (420 g, 0.808 mol) was prepared at 20° C. in THF (2.1 l) and combined with morpholine (105.6 g; 1.213 mol). Nitrogen was conducted into the reaction mixture for 1 h. This was then combined with bis(triphenylphosphine) palladium(II) chloride (284 mg; 0.404 mmol) and triphenylphosphine (424 mg; 1.617 mmol) and the mixture was stirred for 2 h at RT. This was then combined once again with bis(triphenylphosphine)palladium(II) chloride (284 mg; 0.404 mmol) and triphenylphosphine (424 mg; 1.617 mmol) and the mixture was stirred for 2 h at RT. The reaction mixture was added to 4 l of water. It was adjusted to pH=2 with 2 N hydrochloric acid and the resulting crystallizate was stirred overnight. The product was filtered off and washed with water (1.7 l). Drying was carried out at 40° C. in vacuum.

Yield: 575 g (97% of theory) of a beige-colored solid.

MS (ESIpos): m/z (%)=480.0 (100) [M+H]$^+$.

$^1$H-NMR (400 MHz, DMSO-$d_6$): δ=2.12 (s, 3H), 3.48 (s, 3H), 6.32 (s, 1H), 7.12 (s, 1H), 7.72 (m, 2H), 7.80 (m, 1H), 7.88 (br. s, 1H), 8.13 (br. d, 1H), 8.27 (d, 1H), 8.37 (s, 1H), 12.62 (br. s, 1H).

Example 11

(S)-4-[4-cyano-2-(methylsulfonyl)phenyl]-6-methyl-2-oxo-1-[3-(trifluoromethyl)phenyl]-1,2,3,4-tetra-hydropyrimidine-5-carboxylic Acid Quinine Salt (XXIV)

(rac)-4-[4-cyano-2-(methyl sulfonyl)phenyl]-6-methyl-2-oxo-1-[3-trifluoromethyl)phenyl]-1,2,3,4-tetra-hydropyrimidine-5-carboxylic acid (XXII) (563.7 g, 1.176 mol) was prepared at 20° C. in a mixture of isopropanol/water (9:1; 4.2 l) and combined with (−)-quinine (381.4 g; 1.176 mol). This was then heated to 50° C. and stirred for 1 h at 50° C. After cooling to 5° C. it was filtered and the filter cake was washed with a mixture of isopropanol/water (9:1; 1.2 l). Drying was carried out at 40° C. in vacuum.

Yield: 432 g (46% of theory) of a cream-colored solid.

$^1$H-NMR (400 MHz, DMSO-d$_6$): δ=1.58 (m, 2H), 1.79 (m, 1H), 2.04 (m, 1H), 2.10 (s, 3H), 2.33 (m, 1H), 2.79 (m, 1H), 2.90 (m, 2H), 3.21 (m, 1H), 3.33 (m, 2H), 3.46 (s, 3H), 3.90 (s, 3H), 5.11 (d, 1H), 5.14 (d, 1H), 5.53 (br. s, 1H), 6.09 (m, 1H), 6.33 (s, 1H), 7.10 (s, 1H), 7.73 (m, 2H), 7.82 (m, 1H), 7.90 (br. s, 1H), 8.11 (br. d, 1H), 8.27 (d, 1H), 8.44 (s, 1H), 12.70 (br. s, 1H).

Example 12

(S)-4-[4-cyano-2-(methylsulfonyl)phenyl]-6-methyl-2-oxo-1-[3-(trifluoromethyl)phenyl]-1,2,3,4-tetra-hydropyrimidine-5-carboxylic Acid (XI)

(S)-4-[4-cyano-2-(methylsulfonyl)phenyl]-6-methyl-2-oxo-1-[3-(trifluoromethyl)phenyl]-1,2,3,4-tetra-hydropyrimidine-5-carboxylic acid quinine salt (XXIV) (430 g, 0.535 mol) was suspended at 60° C. in a mixture of water (4.2 l) and isopropanol (0.4 l) and adjusted to pH=1 with 2 N hydrochloric acid and stirred for 1 h at 60° C. After cooling to 20° C., filtering was carried out, and the filter cake was washed three times with water (0.6 l). Drying was carried out at 40° C. in vacuum.

Yield: 251 g (98% of theory) of a cream-colored solid.

MS (ESIpos): m/z (%)=480.0 (100) [M+H]$^+$.

$^1$H-NMR (400 MHz, DMSO-d$_6$): δ=2.12 (s, 3H), 3.48 (s, 3H), 6.32 (s, 1H), 7.12 (s, 1H), 7.72 (m, 2H), 7.80 (m, 1H), 7.88 (br. s, 1H), 8.13 (br. d, 1H), 8.27 (d, 1H), 8.37 (s, 1H), 12.62 (br. s, 1H).

Example 13

(S)-4-[4-cyano-2-(methylsulfonyl)phenyl]-6-methyl-2-oxo-1-[3-(trifluoromethyl)phenyl]-1,2,3,4-tetra-hydropyrimidine-5-carboxylic Acid Allyl Ester (X)

(S)-4-[4-cyano-2-(methylsulfonyl)phenyl]-6-methyl-2-oxo-1-[3-(trifluoromethyl)phenyl]-1,2,3,4-tetra-hydropyrimidine-5-carboxylic acid (XI) (250 g, 0.521 mol) was prepared at 20° C. in acetone (1.5 l) and combined with potassium carbonate (72 g; 0.521 mol). After 10 min of stirring, allyl bromide was added (79 g; 652 mol) and the mixture was stirred under reflux for 6 h. After cooling, 1.4 l of water was added to the reaction mixture, and this was stirred for 60 min. The product was filtered off, and washed twice with water (0.6 l) and twice with MtBE (0.6 l). Drying was carried out at 40° C. in vacuum.

Yield: 258 g (95% of theory) of a cream-colored solid.

MS (ESIpos): m/z (%)=534.1 (100) [M+H]$^+$.

$^1$H-NMR (400 MHz, DMSO-ds): δ=2.05 (s, 3H), 2.79 (s, 3H), 3.51 (s, 3H), 4.55 (m, 2H), 5.03 (d, 1H), 5.12 (d, 1H), 5.72 (m, 1H), 6.80 (s, 1H), 7.70 (m, 2H), 7.80 (m, 1H), 7.95 (br. s, 1H), 8.15 (br. d, 1H), 8.25 (d, 1H), 8.52 (s, 1H).

Example 14

(S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylic Acid Allyl Ester (XXIII)

(S)-4-[4-cyano-2-(methyl sulfonyl)phenyl]-6-methyl-2-oxo-1-[3-(trifluoromethyl)phenyl]-1,2,3,4-tetra-hydropyrimidine-5-carboxylic acid allyl ester (X) (250 g, 0.481 mol) was prepared at 20° C. in THF (1.25 l) and combined with a 1 M solution of sodium hexamethyldisilazide (NaHMDS) in THF (102 g; 0.554 mol). After 10 min of stirring, dimethyl sulfate was added (122 g; 0.964 mol) and the mixture was stirred for 2 h at RT. The reaction mixture was added to a solution of 26% aqueous ammonia solution (178 g; 2.4 mol) in 1.5 l of water and rinsed with 200 ml of THF. This was stirred overnight and cooled to 5° C. The product was filtered off and washed with water (0.6 l). Drying was carried out at 40° C. in vacuum.

Yield: 230 g (89% of theory) of a beige-colored solid.

MS (ESIpos): m/z (%)=534.1 (100) [M+H]$^+$.

$^1$H-NMR (400 MHz, DMSO-d$_6$): δ=2.05 (s, 3H), 2.79 (s, 3H), 3.51 (s, 3H), 4.55 (m, 2H), 5.03 (d, 1H), 5.12 (d, 1H), 5.72 (m, 1H), 6.80 (s, 1H), 7.70 (m, 2H), 7.80 (m, 1H), 7.95 (br. s, 1H), 8.15 (br. d, 1H), 8.25 (d, 1H), 8.52 (s, 1H).

Example 15

(R)-4-[4-cyano-2-(methylsulfonyl)phenyl]-6-methyl-2-oxo-1l-[3-(trifluoromethyl)phenyl]-1,2,3,4-tetra-hydropyrimidine-5-carboxylic Acid (XXX)

The combined mother liquors and washing liquors from example 11, containing the quinine salt of (R)-4-[4-cyano-2-(methylsulfonyl)phenyl]-6-methyl-2-oxo-1-[3-(trifluoromethyl)phenyl]-1,2,3,4-tetrahydropyrimidine-5-carboxylic acid (XXV) were concentrated down to a crystal paste. This was taken up in water (5.0 l), adjusted with 2 N hydrochloric acid to pH=1 and stirred for 1 h at 60° C. After cooling to 20° C., filtering was performed, and the filter cake was washed three times with water (1.0 l). Drying was carried out at 40° C. in vacuum.

Yield: 293 g (52% of theory, related to the input of XXII) of a cream-colored solid. Ratio of R-enantiomer to S-enantiomer: 88:12.

MS (ESIpos): m/z (%)=480.0 (100) [M+H]$^+$.

$^1$H-NMR (400 MHz, DMSO-d$_6$): δ=2.12 (s, 3H), 3.48 (s, 3H), 6.32 (s, 1H), 7.12 (s, 1H), 7.72 (m, 2H), 7.80 (m, 1H), 7.88 (br. s, 1H), 8.13 (br. d, 1H), 8.27 (d, 1H), 8.37 (s, 1H), 12.62 (br. s, 1H).

Example 16

(R)-4-[4-cyano-2-(methyl sulfonyl)phenyl]-6-methyl-2-oxo-1-[3-(trifluoromethyl)phenyl]-1,2,3,4-tetra-hydropyrimidine-5-carboxylic Acid Allyl Ester (XXXI)

(R)-4-[4-cyano-2-(methylsulfonyl)phenyl]-6-methyl-2-oxo-1-[3-(trifluoromethyl)phenyl]-1,2,3,4-tetra-hydropy-rimidine-5-carboxylic acid (XXX) (292 g, 0.609 mol) was prepared at 20° C. in acetone (1.6 l) and combined with potassium carbonate (84 g; 0.609 mol). After 10 min of stirring, allyl bromide was added (92 g; 761 mol) and the mixture was stirred under reflux for 6 h. After cooling, 1.5 l of water was added to the reaction mixture and this was stirred for 60 min. The product is filtered off, washed twice with water (0.6 l) and twice with MtBE (0.6 l). Drying is carried out at 40° C. in vacuum.

Yield: 301 g (95% of theory) of a cream-colored solid.
MS (ESIpos): m/z (%)=534.1 (100) [M+H]$^+$.
$^1$H-NMR (400 MHz, DMSO-d$_6$): δ=2.05 (s, 3H), 2.79 (s, 3H), 3.51 (s, 3H), 4.55 (m, 2H), 5.03 (d, 1H), 5.12 (d, 1H), 5.72 (m, 1H), 6.80 (s, 1H), 7.70 (m, 2H), 7.80 (m, 1H), 7.95 (br. s, 1H), 8.15 (br. d, 1H), 8.25 (d, 1H), 8.52 (s, 1H).

Example 17

Isomerization of (R)-4-[4-cyano-2-(methylsulfonyl) phenyl]-6-methyl-2-oxo-1-[3-(trifluoromethyl)phenyl]-1,2,3,4-tetra-hydropyrimidine-5-carboxylic Acid Allyl Ester (XXXI) into (rac)-4-[4-cyano-2-(methylsulfonyl)phenyl]-6-methyl-2-oxo-1-[3-trifluoromethyl)phenyl]-1,2,3,4-tetra-hydropyrimidine-5-carboxylic Acid Allyl Ester (IX)

(R)-4-[4-cyano-2-(methylsulfonyl)phenyl]-6-methyl-2-oxo--[3-(trifluoromethyl)phenyl]-1,2,3,4-tetra-hydropyrimidine-5-carboxylic acid allyl ester (XXXI) (292 g, 0.609 mol) was prepared at 20° C. in acetone (1.6 l) and combined with potassium carbonate (84 g; 0.609 mol). After 10 min of stirring, allyl bromide was added (92 g 761 mol) and the mixture was stirred for 6 h under reflux. After cooling, 1.5 l of water was added to the reaction mixture and the result was stirred for 60 min. The product was filtered off, washed twice with water (0.6 l) and twice with MtBE (0.6 l). Drying was carried out at 40° C. in vacuum.

Yield: 301 g (95% of theory) of a cream-colored solid.
MS (ESIpos): m/z (%)=534.1 (100) [M+H]$^+$.
$^1$H-NMR (400 MHz, DMSO-d$_6$): δ=2.05 (s, 3H), 2.79 (s, 3H), 3.51 (s, 3H), 4.55 (m, 2H), 5.03 (d, 1H), 5.12 (d, 1H), 5.72 (m, 1H), 6.80 (s, 1H), 7.70 (m, 2H), 7.80 (m, 1H), 7.95 (br. s, 1H), 8.15 (br. d, 1H), 8.25 (d, 1H), 8.52 (s, 1H).

Example 18

Physicochemical Characterization of the Compound of Formula (I) in Crystal Form (A)

Parameters of the X-ray diffraction measurement for the compound of formula (I) in crystal form (A):
Device: Transmission diffractometer PANalytical X'Pert PRO with PIXcel counter (multichannel)

| | |
|---|---|
| Scan axis | 2 Theta-Omega |
| Start position [°2Th.] | 2.0000 |
| End position [°2Th.] | 37.9900 |
| Type of divergence diaphragm | fixed |
| Size of divergence diaphragm [°] | 1.0000 |
| Temperature of measurement [° C.] | 25 |
| Anode material | Cu |
| K-Alpha 1 [Å] | 1.54060 |
| Generator setting | 40 mA, 40 kV |
| Diffractometer type | Transmission diffractometer |
| Goniometer radius [mm] | 240.00 |
| Distance between focus and div. diaphragm [mm] | 91.00 |
| Primary beam monochromator | focusing X-ray mirror |
| Sample rotation | yes |

TABLE 1

Peak maxima [2 Theta] of the X-ray diffraction pattern of the compound (I) in crystal form (A)
Peak maximum [2 Theta]
Compound (I), crystal form (A)

7.5
10.0
11.5
11.9
12.2
12.4
13.2
14.7
15.1
15.8
16.0
16.5
17.8
18.5
18.7
19.4
19.8
20.0
20.8
20.9
21.8
22.5
22.9
23.1
23.4
23.5
24.0
24.7
25.1
25.3
25.6
26.5
27.1
27.4
28.0
28.1
28.3
28.7
29.2
29.6
30.3
30.5
30.8
31.7
32.2
32.4
33.4
33.8
34.2
34.5

Measurement Conditions for the Raman Spectroscopy for Measurement of the Compound of Formula (I) in Crystal Form (A):

| | |
|---|---|
| Device | Bruker Raman RFS 100/S |
| Number of Scans | 64 |
| Resolution | 2-4 cm$^{-1}$ |
| Laser Power | 50 mW |
| Laser Wavelength | 1064 mm |

TABLE 2

Band maxima of the Raman spectrum of compound (I) in crystal form (A)
Band maximum [cm−1]
Modification I 3087
3075
3067

TABLE 2-continued

Band maxima of the Raman spectrum of compound (I) in crystal form (A)
Band maximum [cm−1]
Modification I

| |
|---|
| 3044 |
| 3019 |
| 2993 |
| 2969 |
| 2928 |
| 2918 |
| 2236 |
| 2216 |
| 2184 |
| 1646 |
| 1605 |
| 1443 |
| 1435 |
| 1418 |
| 1411 |
| 1395 |
| 1387 |
| 1361 |
| 1354 |
| 1331 |
| 1312 |
| 1299 |
| 1238 |
| 1195 |
| 1169 |
| 1154 |
| 1142 |
| 1091 |
| 1077 |
| 1066 |
| 1056 |
| 1015 |
| 1004 |
| 994 |
| 910 |
| 873 |
| 795 |
| 767 |
| 761 |
| 746 |
| 683 |
| 674 |
| 645 |
| 589 |
| 580 |
| 535 |
| 490 |
| 471 |
| 457 |
| 443 |
| 435 |
| 403 |
| 365 |
| 346 |
| 329 |
| 298 |
| 280 |
| 255 |
| 240 |
| 217 |
| 190 |
| 171 |
| 149 |
| 128 |
| 111 |

DESCRIPTION OF FIGURES

FIG. 1: X-ray diffraction pattern of the compound of formula (I) in crystal form (A)

FIG. 2: Raman spectrum of the compound of formula (I) in crystal form (A).

The invention claimed is:

1. A method for preparing a compound of formula (XXVII)

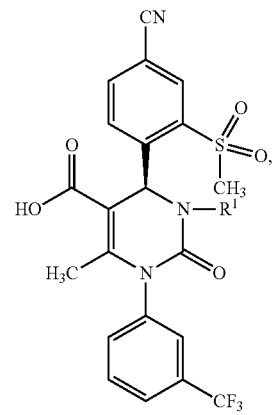

comprising:

a) reacting a compound of formula (XXVI)

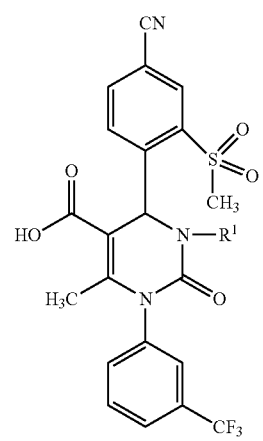

in the presence of a cinchona alkaloid and a solvent to form compounds of formulas (XXVIII) and (XXIX)

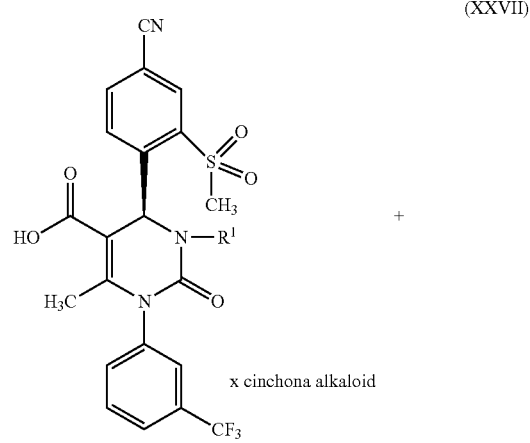

-continued (XXIX)

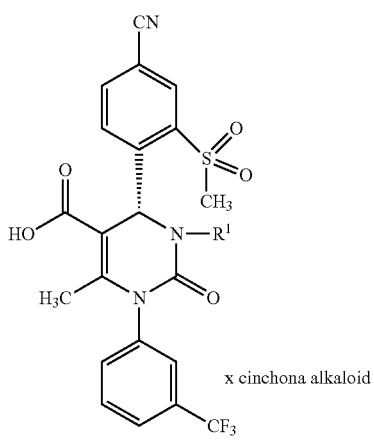

x cinchona alkaloid b) isolating a compound of formula (XXVIII); and
c) reacting the compound of formula (XXVIII) in the presence of a strong acid to form a compound of formula (XXVII), where $R^1$ in the compound of formulas (XXVI), (XXVII), (XXVIII) and (XXIX) is hydrogen or methyl.

2. The method of claim 1, wherein the cinchona alkaloid is chosen from the group consisting of quinine and quinidine.

3. The method of claim 1 wherein $R^1$ in the compound of formulas (XXVI), (XXVII), (XXVIII) and (XXIX) is hydrogen.

4. The method of claim 1 wherein $R^1$ in the compound of formulas (XXVI), (XXVII), (XXVIII) and (XXIX) is methyl.

5. A compound of formula (XXVII)

(XXVII)

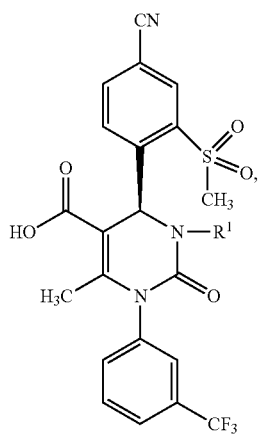

wherein the compound is a quinidine salt and $R^1$ is hydrogen or methyl.

6. The compound of claim 5 wherein $R^1$ is hydrogen.

7. The compound of claim 5 wherein $R^1$ is methyl.

* * * * *

UNITED STATES PATENT AND TRADEMARK OFFICE
CERTIFICATE OF CORRECTION

PATENT NO. : 10,676,443 B2
APPLICATION NO. : 16/394811
DATED : June 9, 2020
INVENTOR(S) : Heiko Schirmer et al.

It is certified that error appears in the above-identified patent and that said Letters Patent is hereby corrected as shown below:

On the Title Page

Item (57), ABSTRACT, please delete "(methyl sulfonyl)phenyl" and insert
-- (methylsulfonyl)phenyl --;

In the Claims

Column 40, Lines 50, Claim 1, please delete "(XXVII)" and insert -- (XXVIII) -- therefor.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*